US008927689B2

(12) United States Patent
Reches et al.

(10) Patent No.: US 8,927,689 B2
(45) Date of Patent: *Jan. 6, 2015

(54) PEPTIDE NANOSTRUCTURES AND METHODS OF GENERATING AND USING THE SAME

(71) Applicant: Ramot at Tel-Aviv University Ltd., Tel-Aviv (IL)

(72) Inventors: Meital Reches, Beit-Hashmonai (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,667

(22) Filed: Nov. 8, 2012

(65) Prior Publication Data

US 2014/0027655 A1 Jan. 30, 2014

Related U.S. Application Data

(60) Continuation of application No. 13/290,147, filed on Nov. 7, 2011, now Pat. No. 8,350,004, which is a division of application No. 12/318,619, filed on Jan. 2, 2009, now Pat. No. 8,053,554, which is a division of application No. 11/148,262, filed on Jun. 9, 2005, now Pat. No. 7,491,699, which is a continuation-in-part of application No. PCT/IL03/01045, filed on Dec. 9, 2003.

(60) Provisional application No. 60/431,709, filed on Dec. 9, 2002, provisional application No. 60/458,378, filed on Mar. 31, 2003, provisional application No. 60/607,588, filed on Sep. 8, 2004, provisional application No. 60/592,523, filed on Aug. 2, 2004.

(51) Int. Cl.

| *A61K 38/04* | (2006.01) |
|---|---|
| *C07K 5/00* | (2006.01) |
| *C07K 7/00* | (2006.01) |
| *C07K 16/00* | (2006.01) |
| *C07K 17/00* | (2006.01) |
| *A61K 38/05* | (2006.01) |
| *H01J 19/24* | (2006.01) |
| *C07K 5/065* | (2006.01) |
| *C07K 5/078* | (2006.01) |
| *C07K 5/06* | (2006.01) |
| *B82Y 5/00* | (2011.01) |
| *B82Y 99/00* | (2011.01) |

(52) U.S. Cl.
CPC ............ *H01J 19/24* (2013.01); *C07K 5/06078* (2013.01); *C07K 5/06156* (2013.01); *C07K 5/06191* (2013.01); *C07K 5/06008* (2013.01); *B82Y 5/00* (2013.01); *B82Y 99/00* (2013.01); Y10S 977/939 (2013.01)
USPC .......................... 530/330; 514/21.91; 977/939

(58) Field of Classification Search
CPC ...... B82Y 5/00; B82Y 99/00; C07K 5/06008; C07K 5/06078; C07K 5/06156; C07K 5/06191; H01J 19/24; Y10S 977/939
See application file for complete search history.

(56) References Cited

U.S. PATENT DOCUMENTS

| 3,042,685 A | 7/1962 | Roussel |
| 2,920,080 A | 1/1965 | Bucourt et al. |
| 3,625,973 A | 12/1971 | Julia |
| 3,790,596 A | 2/1974 | Shkilkova et al. |
| 3,853,987 A | 12/1974 | Dreyer |
| 3,867,517 A | 2/1975 | Ling |
| 3,935,074 A | 1/1976 | Rubenstein et al. |
| 3,976,639 A | 8/1976 | Batcho et al. |
| 3,984,533 A | 10/1976 | Uzgiris |
| 4,036,945 A | 7/1977 | Haber |
| 4,299,917 A | 11/1981 | Berger et al. |
| 4,331,647 A | 5/1982 | Goldenberg |
| 4,626,540 A | 12/1986 | Capps et al. |
| 4,666,828 A | 5/1987 | Gusella |
| 4,801,531 A | 1/1989 | Frossard |
| 4,816,567 A | 3/1989 | Cabilly et al. |
| 4,873,316 A | 10/1989 | Meade et al. |
| 4,925,673 A | 5/1990 | Steiner et al. |
| 4,946,778 A | 8/1990 | Ladner et al. |
| 4,970,233 A | 11/1990 | McHugh |
| 5,013,556 A | 5/1991 | Woodle et al. |
| 5,116,824 A | 5/1992 | Miyata et al. |
| 5,171,505 A | 12/1992 | Lock |
| 5,270,163 A | 12/1993 | Gold et al. |
| 5,272,057 A | 12/1993 | Smulson et al. |

(Continued)

FOREIGN PATENT DOCUMENTS

| DE | 3412445 | 10/1985 |
| DE | 10043282 | 3/2002 |

(Continued)

OTHER PUBLICATIONS

Yan et al. Self-assembly and application of diphenylalanine-based nanostructures. Tutorial Review. Chemical Society Review, 2010 (online publication Mar. 9, 2010), vol. 39, pp. 1877-1890.*
Communication Pursuant to Article 94(3) EPC Dated Dec. 16, 2013 From the European Patent Office Re. Application No. 05747261.5.
Decision to Refuse a European Patent Application Dated Jan. 4, 2013 From the European Patent Office Re. Application No. 06796163.1.
Official Action Dated Jan. 13, 2014 From the US Patent and Trademark Office Re. U.S. Appl. No. 12/083,222.
Official Action Dated Jan. 29, 2013 From the US Patent and Trademark Office Re. U.S. Appl. No. 12/843,097.
Hiemenz "Aggregation", Principles of Colloid and Surface Chemistry, 2nd Ed., Chap.1.7: 27-32, 1986.
Ludtke et al. "Membrane Pores Induced by Magainin", Biochemistry, 35: 13712-13728, 1996.

(Continued)

*Primary Examiner* — Marcela M Cordero Garcia

(57) ABSTRACT

A tubular or spherical nanostructure composed of a plurality of peptides, wherein each of the plurality of peptides includes no more than 4 amino acids and whereas at least one of the 4 amino acids is an aromatic amino acid.

39 Claims, 15 Drawing Sheets
(4 of 15 Drawing Sheet(s) Filed in Color)

(56) References Cited

U.S. PATENT DOCUMENTS

| | | | |
|---|---|---|---|
| 5,304,470 A | 4/1994 | Fischer et al. |
| 5,332,648 A | 7/1994 | Kihara et al. |
| 5,475,096 A | 12/1995 | Gold et al. |
| 5,545,806 A | 8/1996 | Lonberg et al. |
| 5,545,807 A | 8/1996 | Surani et al. |
| 5,567,588 A | 10/1996 | Gold et al. |
| 5,569,825 A | 10/1996 | Lonberg et al. |
| 5,595,877 A | 1/1997 | Gold et al. |
| 5,625,126 A | 4/1997 | Lonberg et al. |
| 5,633,425 A | 5/1997 | Lonberg et al. |
| 5,637,459 A | 6/1997 | Burke et al. |
| 5,643,768 A | 7/1997 | Kawasaki |
| 5,658,754 A | 8/1997 | Kawasaki |
| 5,659,041 A | 8/1997 | Pollak et al. |
| 5,661,016 A | 8/1997 | Lonberg et al. |
| 5,683,867 A | 11/1997 | Biesecker et al. |
| 5,705,337 A | 1/1998 | Gold et al. |
| 5,856,928 A | 1/1999 | Yan |
| 5,916,642 A | 6/1999 | Chang |
| 5,977,302 A | 11/1999 | Palmer et al. |
| 6,110,590 A | 8/2000 | Zarkoob et al. |
| 6,162,828 A | 12/2000 | Fukuda et al. |
| 6,235,876 B1 | 5/2001 | Palmer et al. |
| 6,251,625 B1 | 6/2001 | Bommarius et al. |
| 6,255,286 B1 | 7/2001 | Yanai et al. |
| 6,300,141 B1 | 10/2001 | Segal et al. |
| 6,303,567 B1 | 10/2001 | Findeis et al. |
| 6,309,669 B1 | 10/2001 | Setterstrom et al. |
| 6,326,174 B1 | 12/2001 | Joyce et al. |
| 6,359,112 B2 | 3/2002 | Kapurniotu et al. |
| 6,361,861 B2 | 3/2002 | Gao et al. |
| 6,376,233 B1 | 4/2002 | Wolf et al. |
| 6,472,436 B1 | 10/2002 | Schubert et al. |
| 6,593,339 B1 | 7/2003 | Eek et al. |
| 6,610,478 B1 | 8/2003 | Takle et al. |
| 6,613,875 B1 | 9/2003 | Ghadiri |
| 6,617,114 B1 | 9/2003 | Fowlkes et al. |
| 6,677,153 B2 | 1/2004 | Iversen |
| 6,762,331 B2 | 7/2004 | Hong et al. |
| 6,858,318 B2 | 2/2005 | Kogiso et al. |
| 6,976,639 B2 | 12/2005 | Williams et al. |
| 7,045,537 B1 | 5/2006 | Woolfson et al. |
| 7,491,699 B2 | 2/2009 | Reches et al. |
| 7,504,383 B2 | 3/2009 | Gazit et al. |
| 7,786,086 B2 | 8/2010 | Reches et al. |
| 8,017,586 B2 | 9/2011 | Gazit et al. |
| 8,053,554 B2 | 11/2011 | Reches et al. |
| 8,350,004 B2 * | 1/2013 | Reches et al. ............ 530/300 |
| 8,420,605 B2 | 4/2013 | Ulijn et al. |
| 8,501,697 B2 * | 8/2013 | Gazit et al. ............ 514/21.91 |
| 8,568,637 B2 | 10/2013 | Gazit et al. |
| 2001/0041732 A1 | 11/2001 | Gurley et al. |
| 2002/0006954 A1 | 1/2002 | Hensley et al. |
| 2002/0086067 A1 | 7/2002 | Choi et al. |
| 2002/0151506 A1 | 10/2002 | Castillo et al. |
| 2003/0144185 A1 | 7/2003 | McGimpsey |
| 2003/0158237 A1 | 8/2003 | Saragovi et al. |
| 2003/0211007 A1 | 11/2003 | Maus et al. |
| 2003/0225155 A1 | 12/2003 | Fernandez-Pol et al. |
| 2004/0001893 A1 | 1/2004 | Stupp et al. |
| 2004/0029830 A1 | 2/2004 | Hebert |
| 2004/0052928 A1 | 3/2004 | Gazit |
| 2004/0152672 A1 | 8/2004 | Carson et al. |
| 2004/0258726 A1 | 12/2004 | Stupp et al. |
| 2005/0069950 A1 | 3/2005 | Haynie |
| 2005/0124535 A1 | 6/2005 | McGimpsey |
| 2006/0079454 A1 | 4/2006 | Reches et al. |
| 2006/0079455 A1 | 4/2006 | Gazit et al. |
| 2006/0089380 A1 | 4/2006 | Barnham et al. |
| 2006/0089489 A1 | 4/2006 | Onizuka et al. |
| 2006/0194777 A1 | 8/2006 | Gazit et al. |
| 2006/0234947 A1 | 10/2006 | Gazit |
| 2007/0015813 A1 | 1/2007 | Carter et al. |
| 2007/0021345 A1 | 1/2007 | Gazit |
| 2007/0099840 A1 | 5/2007 | Ulijn et al. |
| 2007/0135334 A1 | 6/2007 | Gazit |
| 2007/0138007 A1 | 6/2007 | Yemini et al. |
| 2007/0298043 A1 | 12/2007 | Gazit et al. |
| 2008/0009434 A1 | 1/2008 | Reches et al. |
| 2009/0061190 A1 | 3/2009 | Gazit et al. |
| 2009/0121709 A1 | 5/2009 | Gazit et al. |
| 2009/0123553 A1 | 5/2009 | Reches et al. |
| 2009/0175785 A1 | 7/2009 | Gazit et al. |
| 2009/0263429 A1 | 10/2009 | Ulijn et al. |
| 2010/0291828 A1 | 11/2010 | Reches et al. |
| 2011/0266517 A1 | 11/2011 | Gazit et al. |
| 2012/0063276 A1 | 3/2012 | Reches et al. |
| 2013/0075703 A1 | 3/2013 | Gazit et al. |
| 2014/0044949 A1 | 2/2014 | Gazit et al. |

FOREIGN PATENT DOCUMENTS

| | | |
|---|---|---|
| EP | 0081122 | 6/1983 |
| EP | 0421946 | 4/1991 |
| EP | 0966975 | 9/2005 |
| EP | 1583713 | 10/2005 |
| FR | 1373316 | 9/1964 |
| JP | 59-044313 | 3/1984 |
| JP | 60-040061 | 3/1985 |
| JP | 63-044895 | 2/1988 |
| JP | 02-295923 | 12/1990 |
| JP | 10-245342 | 9/1998 |
| JP | 2000-193661 | 7/2000 |
| JP | 2007-506732 | 3/2007 |
| WO | WO 80/00789 | 1/1980 |
| WO | WO 97/16191 | 5/1997 |
| WO | WO 98/20135 | 5/1998 |
| WO | WO 99/42102 | 8/1999 |
| WO | WO 99/58652 | 11/1999 |
| WO | WO 00/24390 | 5/2000 |
| WO | WO 01/05421 | 1/2001 |
| WO | WO 01/10457 | 2/2001 |
| WO | WO 01/45726 | 6/2001 |
| WO | WO 01/49307 | 7/2001 |
| WO | WO 02/072086 | 9/2002 |
| WO | WO 02/094857 | 11/2002 |
| WO | WO 03/013442 | 2/2003 |
| WO | WO 03/024443 | 3/2003 |
| WO | WO 03/039540 | 5/2003 |
| WO | WO 03/063760 | 8/2003 |
| WO | WO 03/069033 | 8/2003 |
| WO | WO 03/070269 | 8/2003 |
| WO | WO 03/077866 | 9/2003 |
| WO | WO 2004/050693 | 6/2004 |
| WO | WO 2004/052773 | 6/2004 |
| WO | WO 2004/060791 | 7/2004 |
| WO | WO 2005/016339 | 2/2005 |
| WO | WO 2005/020809 | 3/2005 |
| WO | WO 2005/027901 | 3/2005 |
| WO | WO 2005/031362 | 4/2005 |
| WO | WO 2005/085867 | 9/2005 |
| WO | WO 2006/006172 | 1/2006 |
| WO | WO 2006/013552 | 2/2006 |
| WO | WO 2006/018850 | 2/2006 |
| WO | WO 2006/020681 | 2/2006 |
| WO | WO 2006/027780 | 3/2006 |
| WO | WO 2007/029003 | 3/2007 |
| WO | WO 2007/043048 | 4/2007 |
| WO | WO 01/49281 | 7/2007 |

OTHER PUBLICATIONS

Murphy et al. "Matrix Metalloproteinase Degradation of Elastin, Type IV Collagen and Proteoglycan", Biochemistry Journal, 277: 277-279, 1991.

NCBI "Collagen Type IV A6 Chain [*Homo sapiens*]", GenBank NCBI, GenBank Accession No. AAB19038, Nov. 18, 1996.

Soppimath et al. "Biodegradable Polymeric Nanoparticles as Drug Delivery Devices", Journal of Controlled Release, 70: 1-20, 2001.

Official Action Dated Feb. 8, 2013 From the US Patent and Trademark Office Re. U.S. Appl. No. 11/659,150.

Official Action Dated Mar. 29, 2013 From the US Patent and Trademark Office Re. U.S. Appl. No. 12/083,222.

Ex Parte Quayle Official Action Dated May 17, 2013 From the US Patent and Trademark Office Re. U.S. Appl. No. 11/659,150.

(56) References Cited

OTHER PUBLICATIONS

Official Action Dated Aug. 19, 2013 From the US Patent and Trademark Office Re. U.S. Appl. No. 12/843,097.
Barrett et al. "Multiple Mechanisms for the Carcinogenic Effects of Asbestos and Other Mineral Fibers", Environmental Helath Perspectives, 81: 81-89, 1989.
Lutolf et al. "Cell-Responsive Synthetic Hydrogels", Advanced Materials, 15(11): 888-892, Jun. 5, 2003.
Nishimura et al. "PAR-1 Kinase Plays An Initiator Role in A Temporally Ordered Phosphorylation Process That Confers Tau Toxicity in *Drosophila*", Cell, 116: 671-682, Mar. 5, 2004.
Communication Pursuant to Article 94(3) EPC Dated Jun. 8, 2010 From the European Patent Office Re.: Application No. 06796163.1.
Communication Pursuant to Article 94(3) EPC Dated Aug. 11, 2009 From the European Patent Office Re.: Application No. 05747261.5.
Communication Pursuant to Article 94(3) EPC Dated Jul. 13, 2011 From the European Patent Office Re.: Application No. 05747261.5.
Communication Pursuant to Article 94(3) EPC Dated Nov. 23, 2010 From the European Patent Office Re.: Application No. 09002048.8.
Communication Pursuant to Article 96(2) EPC Dated Jul. 17, 2006 From the European Patent Office Re.: Application No. 03777149.0.
Communication Pursuant to Article 96(2) EPC Dated Jan. 18, 2007 From the European Patent Office Re.: Application No. 04700494.0.
Communication Under Rule 112 EPC Dated Mar. 31, 2006 From the European Patent Office Re.: Application No. 03777149.0.
Examination Report Dated May 10, 2007 From the Government of India, Patent Office Re.: Application No. 1499/CHENP/2005.
Examination Report Dated Jun. 19, 2006 From the Intellectual Property Office of India Re.: Application No. 1510/CHENP/2005.
Examination Report Dated Sep. 23, 2011 From the Government of India, Patent Office, Intellectual Property Building Re. Application No. 915/CHENP/2007.
Examination Report Dated Aug. 29, 2012 From the Government of India, Patent Office, Intellectual Property Building Re. Application No. 915/CHENP/2007.
International Preliminary Report on Patentability Dated Feb. 15, 2007 From the International Bureau of WIPO Re.: Application No. PCT/IL2005/000589.
International Preliminary Report on Patentability Dated Jan. 22, 2009 From the International Bureau of WIPO Re.: Application No. PCT/IL2005/000954.
International Preliminary Report on Patentability Dated Apr. 24, 2008 From the International Bureau of WIPO Re.: Application No. PCT/IL2006/001174.
International Search Report and the Written Opinion Dated Nov. 3, 2006 From the International Searching Authority Re.: Application No. PCT/IL05/00589.
International Search Report and the Written Opinion Dated May 10, 2004 From the International Searching Authority Re.: Application No. PCT/IL2004/000012.
International Search Report and the Written Opinion Dated Jul. 15, 2008 From the International Searching Authority Re.: Application No. PCT/IL05/00954.
International Search Report and the Written Opinion Dated Aug. 22, 2007 From the International Searching Authority Re.: Applicaiton No. PCT/IL2006/001174.
International Search Report Dated Jul. 19, 2004 From the International Searching Authority Re.: Application No. PCT/IL03/01045.
Office Action Dated Jul. 14, 2009 From the Israel Patent Office Re.: Application No. 169121 and Its Translation Into English.
Office Action Dated Sep. 15, 2008 From the Israel Patent Office Re.: Application No. 169120 and Its Translation Into English.
Office Action Dated Sep. 15, 2008 From the Israel Patent Office Re.: Application No. 169121 and Its Translation Into English.
Official Action Dated Apr. 1, 2010 From the US Patent and Trademark Office Re.: U.S. Appl. No. 11/591,613.
Official Action Dated Apr. 3, 2009 From the US Patent and Trademark Office Re.: U.S. Appl. No. 11/662,136.
Official Action Dated Jun. 9, 2010 From the US Patent and Trademark Office Re.: U.S. Appl. No. 11/662,136.
Official Action Dated Dec. 10, 2010 From the US Patent and Trademark Office Re.: U.S. Appl. No. 12/318,619.
Official Action Dated Dec. 11, 2009 From the US Patent and Trademark Office Re.: U.S. Appl. No. 12/318,653.
Official Action Dated Jun. 11, 2012 From the US Patent and Trademark Office Re. U.S. Appl. No. 11/659,150.
Official Action Dated Jan. 12, 2012 From the US Patent and Trademark Office Re. U.S. Appl. No. 13/179,638.
Official Action Dated Oct. 13, 2011 From the US Patent and Trademark Office Re. U.S. Appl. No. 13/179,638.
Official Action Dated Jul. 14, 2008 From the US Patent and Trademark Office Re.: U.S. Appl. No. 11/662,136.
Official Action Dated Feb. 15, 2008 From the US Patent and Trademark Office Re.: U.S. Appl. No. 11/148,262.
Official Action Dated Jul. 15, 2011 From the US Patent and Trademark Office Re. U.S. Appl. No. 12/083,222.
Official Action Dated Mar. 16, 2011 From the US Patent and Trademark Office Re. U.S. Appl. No. 12/083,222.
Official Action Dated Apr. 17, 2012 From the US Patent and Trademark Office Re. U.S. Appl. No. 12/083,222.
Official Action Dated Sep. 19, 2007 From the US Patent and Trademark Office Re.: U.S. Appl. No. 11/148,262.
Official Action Dated Jul. 22, 2010 From the US Patent and Trademark Office Re.: U.S. Appl. No. 12/318,653.
Official Action Dated Jun. 22, 2009 From the US Patent and Trademark Office Re.: U.S. Appl. No. 12/318,653.
Official Action Dated Nov. 26, 2008 From the US Patent and Trademark Office Re.: U.S. Appl. No. 11/662,136.
Official Action Dated Sep. 27, 2007 From the US Patent and Trademark Office Re.: U.S. Appl. No. 11/148,266.
Official Action Dated Apr. 30, 2007 From the US Patent and Trademark Office Re.: U.S. Appl. No. 11/148,262.
Official Action Dated Aug. 30, 2010 From the US Patent and Trademark Office Re.: U.S. Appl. No. 12/318,619.
Official Action Dated Jun. 30, 2010 From the US Patent and Trademark Office Re.: U.S. Appl. No. 11/662,136.
Partial European Search Report and the European Search Opinion Dated Apr. 16, 2009 From the European Patent Office Re.: Application No. 09002048.8.
Summons to Attend Oral Proceedings Pursuant to Rule 115(1) EPC Dated Sep. 13, 2012 From the European Patent Office Re. Application No. 06796163.1.
Summons to Attend Oral Proceedings Pursuant to Rule 115(1) EPC Dated Nov. 30, 2011 From the European Patent Office Re. Application No. 09002048.8.
Supplementary European Search Report Dated Jun. 10, 2009 From the European Patent Office Re.: Application No. 05747261.5.
Ajayan et al. "Application of Carbon Nanotubes", Topics of Applied Physics, 80: 391-425, 2001.
Akazome et al. "Enantioselective Inclusion of Methyl Phenyl Sulfoxides and Benzyl Methyl Sulfoxides by (R)-Phenylglycyl-(R)-Phenylglycine and the Crystal Structures of the Inclusion Cavities", Journal of Organic Chemistry, 65(1): 68-76, 2000.
Altland et al. "Potential Treatment of Transthyretin-Type Amyloidoses by Sulfite", Neurogenetics, 2: 183-188, 1999.
Appukkuttan et al. "Microwave Enhanced Formation of Electron Rich Arylboronates", Synlett, 8: 1204-1206, 2003. Figs., Scheme 4, Compounds 5A, 5B, 5C, 5D.
Azriel et al. "Analysis of the Minimal Amyloid-Forming Fragment of the Islet Amyloid Polypeptide", The Journal of Biological Chemistry, 276(36): 34156-34161, 2001.
Balaram "De Novo Design: Backbone Conformational Constraints in Nucleating Helices and ?-Hairpins", Journal of Peptide Research, 54: 195-199, 1999.
Berson et al. "Proprotein Convertase Cleavage Liberates A Fibrillogenic Fragment of A Resident Glycoprotein to Initiate Melanosome Biogenesis", Journal of Cell Biology, 161(3): 521-533, 2003.
Beugelmans Database Crossfire Beilstein [Online], Beilstein Institut zur F?rderung der Chemischen Wissenschaften, Frankfurt am Main, DE, Database Accession No. 116671 (BRN) Compounds INDOL-2-YL-Methanol & Beugelmans R.: Bulletin de la Soci?t? Chimique Fran?aise, p. 335-336, 1969.

(56) References Cited

OTHER PUBLICATIONS

Bong et al. "Self-Assembling Organic Nanotubes", Angewandte Chemie, International Edition,40:988-1011, 2001.
Changqing et al. "Amyloid-Like Formation by Self-Assembly of Peptidolipids in Two Dimensions", Langmuir, 20: 8641-8645, 2004.
Chapman et al. "Role of *Escherichia coli* Curli Operons in Directing Amyloid Fiber Formation", Science, 295(5556): 851-855, 2002. Abstract.
Cherny et al. "The Formation of *Escherichia coli* Curli Amyloid Fibrils is Mediated by Prion-Like Peptide Repeats", Journal of Molecular Biology, 352(2): 245-252, 2005.
Cherny et al. "The YefM Antitoxin Defines A Family of Natively Unfolded Proteins", The Journal of Biological Chemistry, 279(9): 8252-8261, Feb. 27, 2004.
Chou et al. "Empirical Predictions of Protein Conformation", Annual Reviews in Biochemistry, 47: 251-276, 1978.
Claessen et al. "A Novel Class of Secreted Hydrophodic Proteins Is Involved in Aerial Hyphae Formation in *Streptomyces coelicolor* by Forming Amyloid-Like Fibrils", Genes & Development, 17: 1714-1726, 2003.
Clark et al. "Self-Assembling Cyclic ?3-Peptide Nanotubes as Artificial Transmembrane Ion Channels", Journal of the American Chemical Society, 120: 651-656, 1998.
Cohen et al "Inhibition of Amyloid Fibril Formation and Cytotoxicity by Hydroxyindole Derivatives", Biochemistry, 45: 4727-4735, 2006. p. 4728, col. 1, Last §, p. 4728, col. 2, § 2, p. 4729, col. 1, Last §, col. 2, § 2, Fig.1, 4, p. 4732, col. 2, § 2, 3, p. 4733, col. 2, § 4.
Elliot et al. "The Chaplins: A Family of Hydrophobic Cell-Surface Proteins Involved in Aerial Mycelium Formation in *Streptomyces coelicolor*", Genes & Development, 17: 1727-1740, 2003.
Engelberg-Kulka et al. "Bacterial Programmed Cell Death Systems as Targets for Antibiotics", Trends in Microbiology, XP002477942, 12(2): 66-71, Feb. 2004.
Forloni et al. "Anti-Amyloidogenic Activity of Tetracyclines: Studies In Vitro", FEBS Letters, 487(3): 404-407, 2001. Abstract, Results, Figs.1, 3.
Ganesh et al. "Circular Dichroism and Fourier Transform Infrared Spectroscopic Studies on Self-Assembly of Tetrapeptide Derivative in Solution and Solvated Film", The Journal of Peptide Research: Official Journal of the American Peptide Society, XP002529296, 61(3): 122-128, Mar. 2003.
Gazit "A Possible Role for 'Phi'-Stacking in the Self-Assembly of Amyloid Fibrils", The FASEB Journal, 16: 77-83, 2002.
Gazit "Diversity for Self-Assembly", Nature Chemistry, 2: 1010-1011, Dec. 2010.
Gazit "Mechanisms of Amyloid Fibril Self-Assembly and Inhibition Model Short Peptides as A Key Research Tool", The FEBS Journal, 272: 5971-5978, 2005.
Gazit "Mechanistic Studies of Process of Amyolid Fibrils Formation by the Use of Peptide Fragments and Analogues: Implications for the Design of Fibrillization Inhibitors", Current Medicinal Chemistry, 9: 1725-1735, 2002.
Ghadiri et al. "Artificial Transmembrane Ion Channels From Self-Assembling Peptide Nanotubes", Nature, 369(6478): 301-304, 1994.
Ghadiri et al. "Self-Assembling Organic Nanotubes Based on A Cyclic Peptide Architecture", Nature, XP002936460, 366: 324-327, Dec. 25, 1993.
Goerbitz "Nanotube Formation by Hydrophobic Dipeptides", Chemical European Journal, Chemistry, XP001180634, 7(23): 5153-5159, Dec. 3, 2001.
Gorman et al. "Alzheimer Beta-Amyloid Peptides, Structures of Amyloid Fibrils and Alternate Aggregation Products", Biopolymers, 60: 381-394, 2001.
Grady et al. "Axe-Txe, A Broad-Spectrum Proteic Toxin-Antitoxin System Specified by A Multidrug-Resistant, Clinical Isolate of *Enterococcus faecium*", Molecular Microbiology, 47(5): 1419-1432, 2003. Abstract, p. 1424, col. 1-p. 1426, col. 2, Fig.5.
Grateau "Le Curli du Coli: Une Vari?t? Physiologique d'Amylose [Coli's Curli or How Amyloid Can be Physiological.]", M?decine Sciences, 18(6-7): 664, Jun.-Jul. 2002.

Haldar et al. "First Crystallographic Signature of the Highly Ordered Supramolecular Helical Assemblage From A Tripeptide Containing A Non-Coded Amino Acid", Tetrahedron Letters, XP004343975, 43(14): 2653-2656, 2002. Abstract.
Hartgerink et al. "Peptide Nanotubes and Beyond", Chemistry, XP002276851, 4(8): 1367-1372, 1998.
Hartgerink et al. "Self-Assembling Peptide Nanotubes", Journal of the American Chemical Society, 118: 43-50, 1996.
Hayden et al. "'A' Is for Amylin and Amyloid in Type 2 Diabetes Mellitus", JOP Journal of the Pancreas (Online), 2(4): 124-139, 2001.
Higaki et al. "Regulation of Drug Absorption From Small Intestine by Enteric Nervous System I: A Poorly Absorbable Drug Via Passive Diffusion", Drug Metabolism and Pharmacokinetics, 19(3): 198-205, 2004.
Hirst et al. "Biocatalytic Induction of Supramolecular Order", Nature Chemistry, 2: 1089-1094, Dec. 2010.
Holmes et al. "Extensive Neurite Outgrowth and Active Synapse Formation on Self-Assembling Peptide Scaffolds", Proc. Natl. Acad. Sci. USA, XP002213924, 97(12): 6728-6733, Jun. 6, 2000.
Honma et al. "Use of A Thromboxane A2 Antagonist or Synthase Inhibitor for Treating Central Nervous System Diseases, e.g. Alzheimer Type Dementia," Database WPI, Section Ch. Week 200039, Derwent Publications, AN 2000-451668, Jun. 2, 2000. Abstract. & WO 00/30683.
Horne et al. "A Heterocyclic Peptide Nanotube", Journal of the American Chemical Society, JACS, XP002276671, 125(31): 9372-9376, Aug. 6, 2003. Abstract.
Hoyle et al. "*Pseudomonas aeruginosa* Biofilm as A Diffusion Barrier to Piperacillin", Antimicrobial Agents and Chemotherapy, 36(9): 2054-2056, 1992.
Huang et al. "A Review on Polymer Nanofibers by Electrospinning and Their Applications in Nanocomposites", Composites Science and Technology, 63: 2223-2253, 2003.
Inglot "Comparison of the Antiviral Activity In Vitro of Some Non-Steroidal Anti-Inflammatory Drugs", Journal of General Virology, 4(2): 203-214, 1969.
Jack et al. "The Organization of Aromatic Side Groups in An Amyloid Fibril Probed by Solid-State 2H and 19F NMR Spectroscopy", Journal of the American Chemical Society, JACS, 128: 8098-8099, 2006.
Jayawarna et al. "Nanostructured Hydrogels for Three-Dimensional Cell Culture Through Self-Assembly of Fluorenylmethoxycarbonyl-Dipeptides", Advanced Materials, XP002446151, 18: 611-614, 2006.
Jin "Electrospinning *Bombyx mori* Silk With Poly (Ethylene Oxide)" Biomacromolecules, 3: 1233-1239, 2002.
Kaplan "Fibrous Proteins—Silk as A Model System", Polymer Degradation and Stability, 59: 25-32, 1998.
Kerman et al. "Peptide Nucleic Acid-Modified Carbon Nanotube Field-Effect Transistor for Ultra-Sensitive Real-Time Detection of DNA Hybridization", NanoBiotechnology, 1(1): 65-70, Mar. 2005.
Kimura et al. "Analysis and Prediction of Absorption Profile Including Hepatic First-Pass Metabolism of N-Methyltyramine, A Potent Stimulant of Gastrin Release Present in Beer, After Oral Ingestion in Rats by Gastrointestinal-Transit-Absorption Model", Drug Metabolism and Disposition, 28(5): 577-581, 2000.
Kiselev "Pharmaceutical Composition for Prophylaxis and Treatment of Uterus Cervix Dysplasia and Cancer and Larynx Papillomatosis and Methods of Prophylaxis and Treatment of Said Sicknesses Based on Thereof", Database WPI, Section Ch, Week 200328, Derwent Publications, AN 2003-286683, Jan. 20, 2003. Abstract. & RU 2196568.
Kisilevsky et al. "Arresting Amyloidosis In Vivo Using Small-Molecule Anionic Sulphonates or Sulphates: Implications for Alzheimer's Disease", Nature Medicine, 1: 143-148, 1995. Abstract.
Kocisko et al. "New Inhibitors of Scrabie-Associated Prion Protein Formation in A Library of 2,000 Drugs and Natural Products", Journal of Virology, 77(19): 10288-10294, 2003.
Kon-Ya et al. "Indole Derivatives as Potent Inhibitors of Larval Settlement by the Barnacle, *Balanus amphitrite*", Bioscience, Biotechnology and Biochemistry, 58(12): 2178-2181, 1994. Compound 102.

(56) References Cited

OTHER PUBLICATIONS

Kubik "High-Performance Fibers From Spider Silk", Angewandte Chemie, International Edition, 41(15): 2721-2723, 2002.
Lansbury Jr. "Following Nature's Anti-Amyloid Strategy", Nature Biotechnology, 19(2): 112-113, 2001.
Lashuel et al. "New Class of Inhibitors of Amyloid-? Fibril Formation. Implications for the Mechanism of Pathogenesis in Alzheimer's Disease", The Journal of Biological Chemistry, 277(45): 42881-42890, 2002.
Lazaris et al. "Spider Silk Fibers Spun From Soluble Recombinant Silk Produced in Mammalian Cells", Science, 295: 472-476, 2002. p. 474-475.
Lee et al. "Anti-Diabetic Constituent From the Node of Lotus Rhizome (Nelumbo nucifera Gaertn)", Natural Product Sciences, 7(4), 107-109, 2001.
Lee et al. "Virus-Based Fabrication of Micro- and Nanofibers Using Electrospinnig", Nano Letters, 4(3): 387-390, Mar. 2004.
Li et al. "Amyloid-Like Formation by Self-Assembly of Peptidolipids in Two Dimensions", Langmuir: The ACS Journal of Surfaces and Colloids, XP002529300, 20(20): 8641-8645, Aug. 24-Sep. 28, 2004.
Liao et al. "Triphenylmethane Dyes as Inhibitors of Reverse Transcriptase RNA Polymerase and Protein Synthesis: Structure Activity Relationships", Journal of Medicinal Chemistry, 18(1): 117-120, 1975. Abstract.
Losert et al. "Effect of Indole 3 Alkanecarboxylic Acifs on Glucose Utilization in Rats", Arzneimittel-Forschung/Drug Research, 25(6): 880-887, 1975.
MacPhee et al. "Engineered and Designed Peptide-Based Fibrous Biomaterials", Current Opinion in Solid State and Materials Science, XP002529298, 8(2): 141-149, Mar. 2004.
Mah et al. "A Genetic Basis for *Pseudomonas aeruginosa* Biofilm Antibiotic Resistance", Nature, 426: 306-310, 2003.
Mahler et al. "Rigid, Self-Assembled Hydrogel Composed of A Modified Aromatic Dipeptide", Advanced Materials, XP002446150, 18(11): 1365-1370, 2006.
Maji et al. "Fibril-Forming Model Synthetic Peptides Containing 3-Aminophenylacetic Acid", Tetrahedron, XP004390176, 58(43): 8695-8702, 2002.
Martin et al. "The Emerging Field of Nanotube Biotechnology", Nature Reviews: Drug Discovery, 2(1): 29-37, Jan. 2003. Abstract.
Matsui et al. "Crystalline Glyclylglycine Bolaamphiphile Tubules and Their pH-Sensitive Structural Transformation" The Journal of Physical Chemistry B, 104(15): 3384-3386, 2000.
Meluleni et al. "Mucoid *Pseudomonas aeruginosa* Growing in A Biofilm in Vitro Are Killed by Opsonic Antibodies to the Mucoid Exopolysaccharide Capsule But Not by Antibodies Produced During Chronic Lung Infection in Cystic Fibrosis Patients,", Journal of Immunology, 155: 2029-2038, 1995.
Murphy et al. "Biofilm Formation by Nontypeable *Haemophilus influenzae*: Strain Variability, Outer Membrane Antigen Expression and Role of Pili", BMC Microbiology, 2(7): 1471-2180, 2002.
Nakajima "Amine Precursor Therapy: Manipulation of Brain Amine Activity With Precursor Amino Acid", Psychiatry and Clinical Neurosciences, 51(5), 267-274, 1997. p. 269, col. 1, § 2, 3.
Oza et al. "Synthesis and Evaluation of Anthranilic Acid-Based Transthyretin Amyloid Fibril Inhibitors", Bioorganic & Medicinal Chemistry Letters 9(1): 1-6, 1999.
Pavia et al. "Antimicrobial Activity of Nicotine Against A Spectrum of Bacterial and Fungal Pathogens", Journal of Medical Microbiology, 49(7): 675-676, 2000.
Perutz et al. "Amyloid Fibers Are Water-Filled Nanotubes", Proc. Natl. Acad. Sci. USA, PNAS, 99(8): 5591-5595, Apr. 16, 2002.
Peterson et al. "Inhibiting Transthyretin Conformational Chamges That Lead to Amyloid Fibril Formation", Proc. Natl. Acad. Sci. USA, 95: 12956-12960, 1998.
Pispisa et al. "A Spectroscopic and Molecular Mechanics Investigation on A Series of AIB-Based Linear Peptides and A Peptide Template, Both Containing Tryptophan and A Nitroxide Derivative as Probes", Biopolymers, 53: 169-181, 2000.
Rajagopal et al. "Self-Assembling Peptides and Proteins for Nanotechnological Applications", Current Opinion in Structural Biology, XP002529297, 14(4): 480-486, Aug. 2004.
Reches et al. "Amyloid Fibril Formation by Pentapeptide and Tetrapeptide Fragments of Human Calcitonin", The Journal of Biological Chemistry, XP002276670, 277(38): 35475-35480, 2002.
Reches et al. "Casting Metal Nanowires Within Discrete Self-Assembled Peptide Nanotubes", Science, XP002276672, 300(5619): 625-627, Apr. 25, 2003. "Supporting Online Materials", Science [Online], 300(5619): 1-9, Apr. 25, 2003.
Reches et al. "Designed Aromatic Homo-Dipeptides: Formation of Ordered Nanostructures and Potential Nanotechnological Applications", Physical Biology, 3: S10-S19, 2006.
Reches et al. "Formation of Closed-Cage Nanostructures by Self-Assembly of Aromatic Dipeptides", Nano Letters, 4(4): 581-585, 2004.
Reches et al. "Self-Assembly of Peptide Nanotubes and Amyloid-Like Structures by Charged-Termini-Capped Diphenylalanine Peptide Analogues", Israel Journal of Chemistry, XP009087914, 45(3): 363-371, Jun. 30, 2005.
Reches et al. "Supporting Online Material", Science, 300(5619): 1-9, Apr. 25, 2003.
Robinson et al. "The Design of A Biochip: A Self-Assembling Molecular-Scale Memory", Protein Engineering, 1(4): 295-300, 1987.
Ryadnov et al. "Engineering the Morphology of A Self-Assembling Protein Fibre", Nature Materials, XP002529299, 2(5): 329-332, May 2003.
Sacchettini et al. "Therapeutic Strategies for Human Amyloid Diseases", Nature Reviews: Drug Discovery, 1: 267-275, 2002.
Soto et al. "Beta-Sheet Breaker Peptides Inhibit Fibrillogenesis in a Rat Brain Model of Amyloidosis: Implications for Alzheimer's Therapy", Nature Medicine 4(7): 822-826, 1998.
Stephenson et al. "The 'Promiscuous Drug Concept' With Applications to Alzheimer's Disease", FEBS Letters, 579: 1338-1342, 2005.
Stewart "Theoretical Aspects of Antibiotic Diffusion Into Microbial Biofilms", Antimicrobial Agents and Chemotherapy, 40(11): 2517-2522, 1996.
Toledano et al. "Enzyme-Triggered Self-Assembly of Peptide Hydrogels Via Reversed Hydrolysis", Journal of the American Chemical Society, JACS, XP002421984, 128(4): 1070-1071, Feb. 1, 2006.
True et al. "Epigenetic Regulation of Trenslation Reveals Hidden Genetic Variation to Produce Complex Traits", Nature, 431: 184-187, 2004.
Tsai et al. "Synthesis of AIB-Containing Peptidomimetics as Potential Inhibitors of Alzheimer's Gamma-Secretase", 218th ACS National Meeting, New Orleans, USA, Meeting Abstract, MEDI-018, 1999. Abstract.
Tsang et al. "A Simple Chemical Method of Opening and Filling Carbon Nanotubes", Nature, 372: 159-162, 1994.
Tuite et al. "Propagation of Yeast Prions", Nature Reviews, 4: 878-889, 2003.
Vauthey et al. "Molecular Self-Assembly of Surfactant-Like Peptides to Form Nanotubes and Nanovesicles", Proc. Natl. Acad. Sci. USA, 99(8): 5355-5360, 2002.
Westwater et al. "Use of Genetically Engineered Phage to Deliver Antimicrobial Agents to Bacteria: An Alternative Therapy for Treatment of Bacterial Infections", Antimicrobial Agents and Chemotherapy, 47 (4): 1301-1307, 2003.
Yan et al. "Self-Assembling and Application of Diphenylalanine-Based Nanostructures", Chemical Society Reviews, 39: 1877-1890, 2010.
Yokoi et al. "Dynamic Reassembly of Peptide RADA16 Nanofiber Scaffold", Proc. Natl. Acad. Sci. USA, XP002446152, 102(24): 8414-8419, Jun. 2005.
Zhang "Fabrication of Novel Biomaterials Through Molecular Self-Assembly", Nature Biotechnology, XP002305982, 21(10): 1171-1178, Oct. 1, 2003. p. 1172-1173, p. 1173, Right col., p. 1174.

(56) References Cited

OTHER PUBLICATIONS

Zhang et al. "Design of Nanostructured Biological Materials Through Self-Assembly of Peptides and Proteins", Current Opinion in Chemical Biology, 6: 865-871, 2002.

Zhang et al. "Supramolecular Hydrogels Respond to Ligand-Receptor Interaction", Journal of the American Chemical Society, XP002421981, 125(45): 13680-13681, Nov. 12, 2003.

Zhao et al. "Fabrication of Molecular Materials Using Peptide Construction Motifs", Trends in Biotechnology, XP004552612, 22(9): 470-476, Sep. 1, 2004.

Applicant-Initiated Interview Summary Dated Oct. 11, 2013 From the US Patent and Trademark Office Re. U.S. Appl. No. 12/843,097.

Notification of Non-Compliant Appeal Brief (37 CFR 41.37) Dated Jun. 19, 2014 From the US Patent and Trademark Office Re. U.S. Appl. No. 12/083,222.

* cited by examiner

SEQ ID NO: 14  KLVFFAE  former
SEQ ID NO: 15  KLVFF    inhibitor
SEQ ID NO: 16  LVFFA    inhibitor

SEQ ID NO: 17
NH$_2$-DAEFRHDSGYEVHHQKLVFFAEDVGSNKGAIIGLMVGGVVIA-COOH

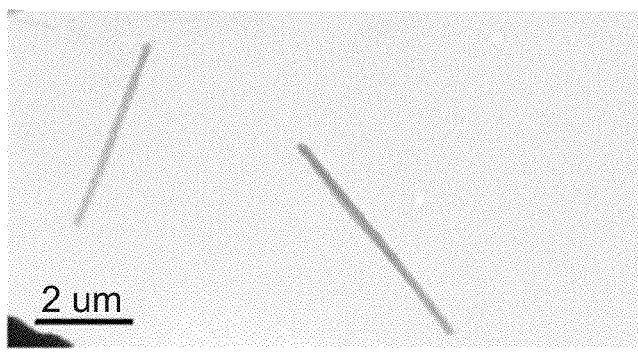
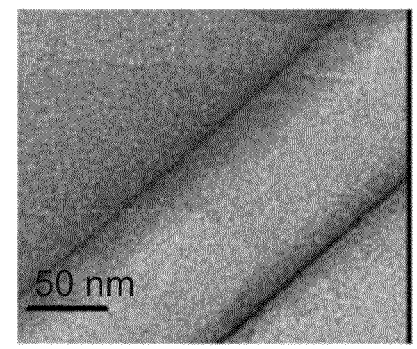
Fig. 10a　　　　　　　　Fig. 10b
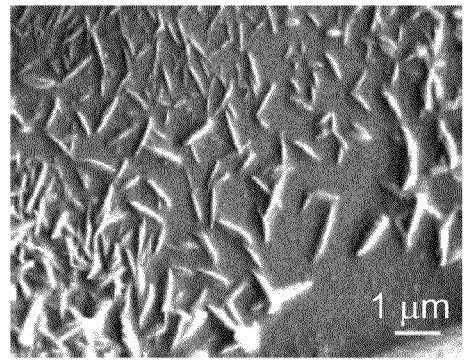
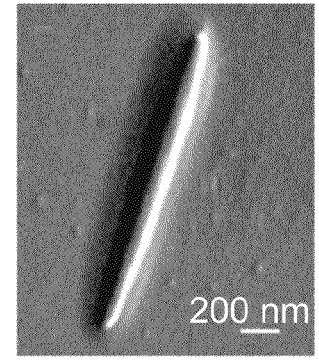
Fig. 11a　　　　　　　　Fig. 11b
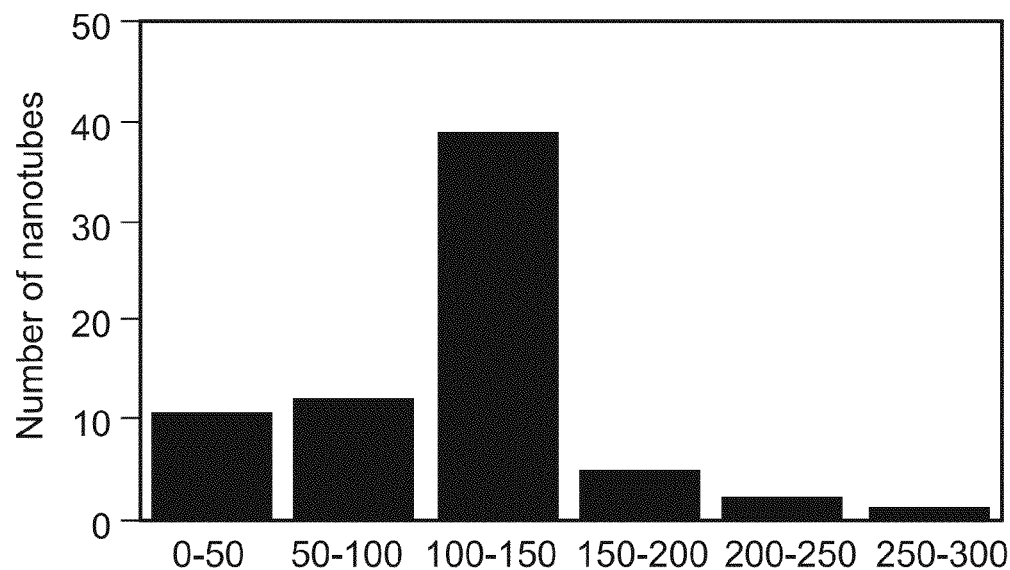
Fig. 11c NH$_2$-D-Phe-D-Phe-COOH
+Proteinase K NH$_2$-L-Phe-L-Trp-COOH

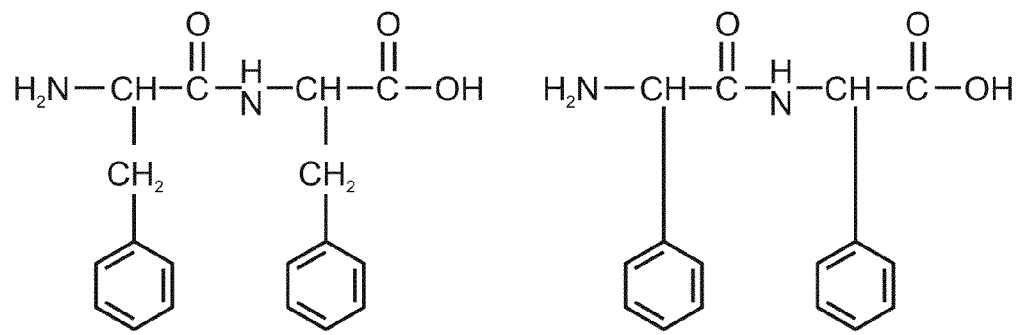
NH$_2$-Phe-Phe-COOH
Fig. 15a
NH$_2$-Phg-Phg-COOH
Fig. 15b
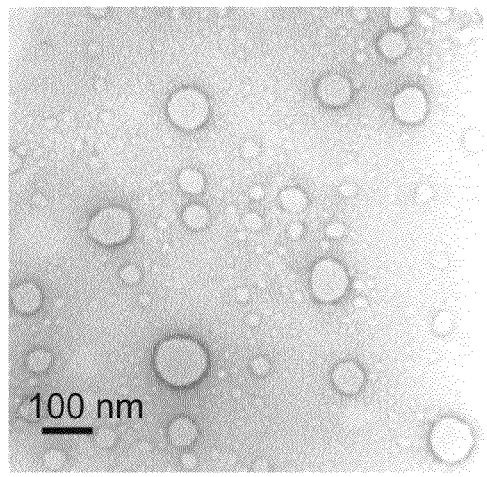
Fig. 15c
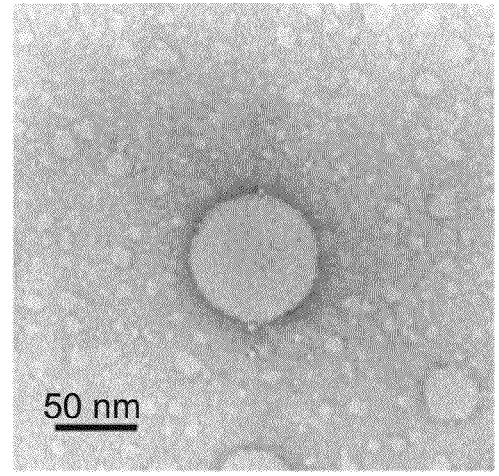
Fig. 15d

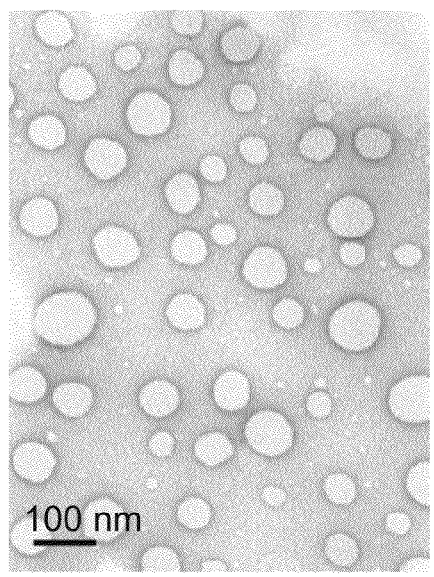 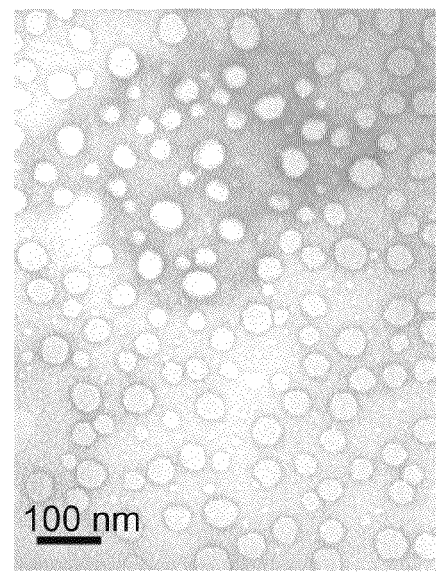
Phg-Phg+10%TFA
Phg-Phg+1M NaOH
Fig. 17a
Fig. 17b

PEPTIDE NANOSTRUCTURES AND METHODS OF GENERATING AND USING THE SAME

RELATED APPLICATIONS

This application is a continuation of U.S. patent application Ser. No. 13/290,147 filed on Nov. 7, 2011, which is a divisional of U.S. patent application Ser. No. 12/318,619 filed on Jan. 2, 2009, now U.S. Pat. No. 8,053,554, which is a divisional of U.S. patent application Ser. No. 11/148,262 filed on Jun. 9, 2005, now U.S. Pat. No. 7,491,699, which is a continuation-in-part (CIP) of PCT Patent Application No. PCT/IL03/01045 filed on Dec. 9, 2003, which claims the benefit of priority under 35 USC 119(e) of U.S. Provisional Patent Application Nos. 60/431,709 filed on Dec. 9, 2002 and 60/458,378 filed on Mar. 31, 2003.

U.S. patent application Ser. No. 11/148,262 also claims the benefit of priority under 35 USC 119(e) of U.S. Provisional Patent Application Nos. 60/607,588 filed on Sep. 8, 2004 and 60/592,523 filed on Aug. 2, 2004.

The contents of all of the above applications are incorporated by reference as if fully set forth herein.

FIELD AND BACKGROUND OF THE INVENTION

The present invention relates to peptide nanostructures and methods of generating and using same.

Nanoscience is the science of small particles of materials and is one of the most important research frontiers in modern technology. These small particles are of interest from a fundamental point of view since they enable construction of materials and structures of well-defined properties. With the ability to precisely control material properties come new opportunities for technological and commercial development, and applications of nanoparticles have been shown or proposed in areas as diverse as micro- and nanoelectronics, nanofluidics, coatings and paints and biotechnology.

Numerous configurations have been proposed and applied for the construction of nanostructures. Most widely used are the fullerene carbon nanotubes. Two major forms of carbon nanotubes exist, single-walled nanotubes (SWNT), which can be considered as long wrapped graphene sheets and multi walled nanotubes (MWNT) which can be considered as a collection of concentric SWNTs with different diameters.

SWNTs have a typical length to diameter ratio of about 1000 and as such are typically considered nearly one-dimensional. These nanotubes consist of two separate regions with different physical and chemical properties. A first such region is the side wall of the tube and a second region is the end cap of the tube. The end cap structure is similar to a derived from smaller fullerene, such as $C_{60}$.

Carbon nanotubes produced to date suffer from major structural limitations. Structural deviations including Y branches, T branches or SWNT junctions, are frequent results of currently used synthesis processes. Though such deviations in structure can be introduced in a "controlled" manner under specific conditions, frequent uncontrollable insertion of such defects result in spatial structures with unpredictable electronic, molecular and structural properties.

Other well-studied nanostructures are lipid surfactant nanomaterials (e.g., diacetylene lipids) which self-assemble into well-ordered nanotubes and other bilayer assemblies in water and aqueous solution [Yager (1984) Mol. Cryst. Liq. Cryst. 106:371-381; Schnur (1993) Science 262:1669-1676; Selinger (2001) J. Phys. Chem. B 105:7157-7169]. One proposed application of lipid tubules is as vehicles for controlled drug release. Accordingly, such tubes coated with metallic copper and loaded with antibiotics were used to prevent marine fouling.

Although lipid-based nanotubules are simple in form, lipid structures are mechanically weak and difficult to modify and functionalize, thus restricting their range of applications.

Recently, peptide building blocks have been shown to form nanotubes. Peptide-based nanotubular structures have been made through stacking of cyclic D-, L-peptide subunits. These peptides self-assemble through hydrogen-bonding interactions into nanotubules, which in-turn self-assemble into ordered parallel arrays of nanotubes. The number of amino acids in the ring determines the inside diameter of the nanotubes obtained. Such nanotubes have been shown to form transmembrane channels capable of transporting ions and small molecules [Ghadiri, M. R. et al., Nature 366, 324-327 (1993); Ghadiri, M. R. et al., Nature 369, 301-304 (1994); Bong, D. T. et al., Angew. Chem. Int. Ed. 40, 988-1011 (2001)].

More recently, the discovery of surfactant-like peptides that undergo spontaneous assembly to form nanotubes with a helical twist has been made. The monomers of these surfactant peptides, like lipids, have distinctive polar and nonpolar portions. They are composed of 7-8 residues, approximately 2 nm in length when fully extended, and dimensionally similar to phospholipids found in cell membranes. Although the sequences of these peptides are diverse, they share a common chemical property, i.e., a hydrophobic tail and a hydrophilic head. These peptide nanotubes, like carbon and lipid nanotubes, also have a very high surface area to weight ratio. Molecular modeling of the peptide nanotubes suggests a possible structural organization [Vauthey (2002) Proc. Natl. Acad. Sci. USA 99:5355; Zhang (2002) Curr. Opin. Chem. Biol. 6:865]. Based on observation and calculation, it is proposed that the cylindrical subunits are formed from surfactant peptides that self-assemble into bilayers, where hydrophilic head groups remain exposed to the aqueous medium. Finally, the tubular arrays undergo self-assembly through non-covalent interactions that are widely found in surfactant and micelle structures and formation processes.

Peptide based bis(N-α-amido-glycyglycine)-1,7-heptane dicarboxylate molecules were also shown to be assembled into tubular structures [Matsui (2000) J. Phys. Chem. B 104: 3383].

When the crystal structure of di-phenylalanine peptides was determined, it was noted that hollow nanometric channels are formed within the framework of the macroscopic crystal [Gorbitz (2001) Chemistry 7(23):5153-9]. However, no individual nanotubes could be formed by crystallization, as the crystallization conditions used in this study included evaporation of an aqueous solution at 80° C. No formation of discrete nano-structures was reported under these conditions.

As mentioned hereinabove, peptide nanotubes contributed to a significant progress in the field of nanotechnology since such building blocks can be easily modified and used in numerous mechanical, electrical, chemical, optical and biotechnological systems.

The development of systems which include nanoscale components has been slowed by the unavailability of devices for sensing, measuring and analyzing with nanometer resolution. One class of devices that have found some use in nanotechnology applications are proximity probes of various types including those used in scanning tunneling microscopes, atomic force microscopes and magnetic force microscopes. While good progress has been made in controlling the position of the macroscopic probe to sub-angstrom accuracy and in designing sensitive detection schemes, the tip designs to date have a number of problems.

One such problem arises from changes in the properties of the tip as atoms move about on the tip, or as the tip acquires an atom or molecule from the object being imaged. Another difficulty with existing probe microscope tips is that they typically are pyramidal in shape, and that they are not able to penetrate small openings on the object being imaged. Moreover, existing probe microscopes often give false image information around sharp vertical discontinuities (e.g., steps) in the object being imaged, because the active portion of the tip may shift from the bottom atom to an atom on the tip's side.

An additional area in which nanoscience can play a role is related to heat transfer. Despite considerable previous research and development focusing on industrial heat transfer requirements, major improvements in cooling capabilities have been held back because of a fundamental limit in the heat transfer properties of conventional fluids. It is well known that materials in solid form have orders-of-magnitude larger thermal conductivities than those of fluids. Therefore, fluids containing suspended solid particles are expected to display significantly enhanced thermal conductivities relative to conventional heat transfer fluids.

Low thermal conductivity is a primary limitation in the development of energy-efficient heat transfer fluids required in many industrial applications. To overcome this limitation, a new class of heat transfer fluids called nanofluids has been developed by suspending nanocrystalline particles in liquids such as water, oil, or ethylene glycol. The resulting nanofluids possess extremely high thermal conductivities compared to the liquids without dispersed nanocrystalline particles. Excellent suspension properties are also observed, with no significant settling of nanocrystalline oxide particles occurring in stationary fluids over time periods longer than several days. Direct evaporation of copper nanoparticles into pump oil results in similar improvements in thermal conductivity compared to oxide-in-water systems, but importantly, requires far smaller concentrations of dispersed nanocrystalline powder.

Numerous theoretical and experimental studies of the effective thermal conductivity of dispersions containing particles have been conducted since Maxwell's theoretical work was published more than 100 years ago. However, all previous studies of the thermal conductivity of suspensions have been confined to those containing millimeter- or micron-sized particles. Maxwell's model shows that the effective thermal conductivity of suspensions containing spherical particles increases with the volume fraction of the solid particles. It is also known that the thermal conductivity of suspensions increases with the ratio of the surface area to volume of the particle. Since the surface area to volume ratio is 1000 times larger for particles with a 10 nm diameter than for particles with a 10 mm diameter, a much more dramatic improvement in effective thermal conductivity is expected as a result of decreasing the particle size in a solution than can obtained by altering the particle shapes of large particles.

It is recognized that peptide nanotubes are natural candidates for performing the above and many other tasks in the field of nanotechnology.

However, currently available peptide nanotubes are composed of peptide building blocks, which are relatively long and as such are expensive and difficult to produce, or limited by heterogeneity of structures that are formed as bundles or networks rather than discrete nanoscale structures.

There is thus a widely recognized need for, and it would be highly advantageous to have, a peptide nanostructure, which is devoid of the above limitations.

SUMMARY OF THE INVENTION

According to one aspect of the present invention there is provided a tubular, spherical or planar nanostructure composed of a plurality of peptides, wherein each of the plurality of peptides includes at least one aromatic amino acid in the case of peptides that consists of no more than 4 amino acids and aromatic polypeptides which are composed solely from aromatic amino acids.

According to another aspect of the present invention there is provided a method of generating a tubular, spherical or planar nanostructure, the method comprising incubating a plurality of peptide molecules under conditions which favor formation of the tubular, spherical or planar nanostructure, wherein each of the peptide molecules includes no more than 4 amino acids and whereas at least one of the 4 amino acids is an aromatic amino acid.

According to further features in preferred embodiments of the invention described below, the conditions which favor formation the tubular, spherical or planar nanostructure are selected from the group consisting of a solution type, concentration of the peptide molecules, aggregation time, non-evaporating conditions and temperature.

According to yet another aspect of the present invention there is provided a field emitter device, comprising an electrode and a nanostructure being composed of a plurality of peptides, the electrode and the nanostructure being designed and constructed such that when an electrical field is formed therebetween, electrons are emitted from the nanostructure, wherein each of the plurality of peptides of the nanostructure includes no more than 4 amino acids and wherein at least one of the 4 amino acids is an aromatic amino acid.

According to further features in preferred embodiments of the invention described below, the field emitter device further comprises a substrate having a fluorescent powder coating, the fluorescent powder coating being capable of emitting light upon activation by the electrons.

According to still another aspect of the present invention there is provided a device for obtaining information from a nanoscale environment, the device comprising: (a) a nanostructure capable of collecting signals from the nanoscale environment, the nanostructure being composed of a plurality of peptides each including no more than 4 amino acids, wherein at least one of the 4 amino acids is an aromatic amino acid; and (b) a detection system capable of interfacing with the nanostructure and receiving the signals thus obtaining information from the nanoscale environment.

According to further features in preferred embodiments of the invention described below, the device for obtaining information further comprises a supporting element onto which the nanostructure being mounted, wherein the supporting element is operable to physically scan the nanoscale environment.

According to still further features in the described preferred embodiments the nanostructure is adapted to collect near field light from the nanoscale environment.

According to still further features in the described preferred embodiments the detection system is capable of converting physical motion of the nanostructure to electric signals.

According to an additional aspect of the present invention there is provided an apparatus for electron emission lithography, comprising: (a) an electron emission source being at a first electrical potential, the electron emission source including at least one nanostructure being composed of a plurality of peptides each including no more than 4 amino acids, wherein at least one of the 4 amino acids is an aromatic amino acid;

and (b) an electrically conducting mounting device being in a second electrical potential, the second electrical potential being different than the first electrical potential; wherein a difference between the second electrical potential and the first electrical potential is selected such that electrons are emitted from the electron emission source, and impinge on the mounting device to thereby perform a lithography process on a sample mounted on the mounting device.

According to further features in preferred embodiments of the invention described below, the apparatus further comprises a magnetic field generator for generating a magnetic field, thereby to direct the electrons to a predetermined location on the sample.

According to yet an additional aspect of the present invention there is provided a memory cell, comprising: (a) an electrode; and (b) a nanostructure composed of a plurality of peptides each including no more than 4 amino acids at least one of which being an aromatic amino acid, the nanostructure being capable of assuming one of at least two states; the nanostructure and the electrode being designed and constructed such that when electrical current flows through the electrode, the nanostructure transforms from a first state of the at least to states to a second state of the at least to states.

According to further features in preferred embodiments of the invention described below, the transformation from the first state to the second state comprises a geometrical deflection of the nanostructure.

According to still an additional aspect of the present invention there is provided a mechanical transmission device, comprising a first nanostructure and a second nanostructure, the first and the second nanostructure being operatively associated thereamongst such that a motion of the first nanostructure generates a motion of the second nanostructure, wherein at least one of the first and the second nanostructures is composed of a plurality of peptides each includes no more than 4 amino acids, wherein at least one of the 4 amino acids is an aromatic amino acid.

According to a further aspect of the present invention there is provided a nanoscale mechanical device, comprising at least one nanostructure designed and configured for grabbing and/or manipulating nanoscale objects, wherein the at least one nanostructures is composed of a plurality of peptides each including no more than 4 amino acids, wherein at least one of the 4 amino acids is an aromatic amino acid.

According to further features in preferred embodiments of the invention described below, the device further comprises a voltage source for generating electrostatic force between the first and the second tubular nanostructures, thereby to close or open the first and the second tubular nanostructures on the nanoscale object.

According to yet a further aspect of the present invention there is provided an electronic switching or amplifying device comprising a source electrode, a drain electrode, a gate electrode and a channel, wherein at least one of the gate electrode and the channel comprises a nanostructure being composed of a plurality of peptides each including no more than 4 amino acids, wherein at least one of the 4 amino acids is an aromatic amino acid.

According to still a further aspect of the present invention there is provided an electronic inverter having a first switching device and a second switching device, each of the first switching device and the first switching device comprising a source electrode, a drain electrode, a gate electrode and a channel, such that the a drain electrode of the first switching device is electrically communicating with the source electrode of the second switching device, wherein at least one of the gate electrode and the channel comprises a nanostructure being composed of a plurality of peptides each including no more than 4 amino acids, wherein at least one of the 4 amino acids is an aromatic amino acid.

According to still further features in the described preferred embodiments the source electrode and the drain electrode are formed on a substrate.

According to still further features in the described preferred embodiments the substrate comprises a thermal oxide deposited over a silicon substrate.

According to still a further aspect of the present invention there is provided a composition, comprising a polymer and a nanostructure, the nanostructure being composed of a plurality of peptides, each including no more than 4 amino acids, wherein at least one of the 4 amino acids is an aromatic amino acid.

According to still a further aspect of the present invention there is provided a composition, comprising a matrix and a plurality of nanostructures dispersed throughout the matrix, the nanostructure being composed of a plurality of peptides, each including no more than 4 amino acids, wherein at least one of the 4 amino acids is an aromatic amino acid.

According to further features in preferred embodiments of the invention described below, the matrix is selected from the group consisting of a metal matrix, a ceramic matrix and a polymeric matrix.

According to still further features in the described preferred embodiments the matrix is a two-dimensional matrix.

According to still further features in the described preferred embodiments the matrix is a three-dimensional matrix.

According to still a further aspect of the present invention there is provided a nanofluid comprising nanostructures suspended in a fluid, wherein at least a portion of the nanostructures is composed of a plurality of peptides, each including no more than 4 amino acids, wherein at least one of the 4 amino acids is an aromatic amino acid.

According to still a further aspect of the present invention there is provided a heat transfer device, comprising a nanofluid and a channel for holding the nanofluid, the nanofluid comprising nanostructures suspended in a fluid, wherein at least a portion of the nanostructures is composed of a plurality of peptides, each including no more than 4 amino acids, wherein at least one of the 4 amino acids is an aromatic amino acid, the nanofluid and the channel being designed and constructed such that heat is carried by the nanostructures from a first end of the channel to a second end thereof.

According to further features in preferred embodiments of the invention described below, the heat transfer device further comprises a locomotion system for generating locomotion of the nanofluid within the channel.

According to still a further aspect of the present invention there is provided a method of emitting electrons, the method forming an electric field near a nanostructure being composed of a plurality of peptides, such that electrons are emitted therefrom, wherein each of the plurality of peptides of the nanostructure includes no more than 4 amino acids and wherein at least one of the 4 amino acids is an aromatic amino acid.

According to still a further aspect of the present invention there is provided a method of obtaining information from a nanoscale environment, the method comprising: (a) collecting signals from the nanoscale environment using a nanostructure, the nanostructure being composed of a plurality of peptides each including no more than 4 amino acids, wherein at least one of the 4 amino acids is an aromatic amino acid; and (b) receiving the signals from the nanostructure, thus obtaining information from the nanoscale environment.

According to further features in preferred embodiments of the invention described below, the method further comprising physically scanning the nanoscale environment using the nanostructure.

According to still further features in the described preferred embodiments the information signals are selected from the group consisting of mechanical signals, optical signals, electrical signals, magnetic signals, and chemical signals.

According to still further features in the described preferred embodiments the information signals comprise near field light from the nanoscale environment.

According to still further features in the described preferred embodiments the method further comprises converting physical motion of the nanostructure to electric signals.

According to still a further aspect of the present invention there is provided a method of electron emission lithography, the method comprising: (a) using an electron emission source for emitting electrons, the electron emission source including at least one nanostructure being composed of a plurality of peptides each including no more than 4 amino acids, wherein at least one of the 4 amino acids is an aromatic amino acid; and (b) collecting the electrons on an electrically conducting mounting device, thereby performing a lithography process on a sample mounted on the mounting device.

According to still further features in the described preferred embodiments the method further comprises generating a magnetic field to thereby direct the electrons to a predetermined location on the sample.

According to still a further aspect of the present invention there is provided a method of recording binary information, the binary information being composed of a first type of datum and a second type of datum, the method comprising using a plurality of nanostructure each capable of assuming one of two states, wherein a first state of the two states correspond to the first type of datum and the second state of the two states correspond to the second type of datum; wherein each of the plurality of nanostructures is composed of a plurality of peptides each including no more than 4 amino acids at least one of which being an aromatic amino acid.

According to still a further aspect of the present invention there is provided a method of transmitting mechanical motion, the method comprising: (a) providing a first nanostructure and a second nanostructure, at least one of the first and the second nanostructures is composed of a plurality of peptides each includes no more than 4 amino acids, wherein at least one of the 4 amino acids is an aromatic amino acid; and (b) generating a motion of the first nanostructure such that the motion of the first nanostructure generates a motion of the second nanostructure.

According to still a further aspect of the present invention there is provided a method of grabbing and/or manipulating nanoscale objects, the method comprising: (a) providing at least one nanostructure composed of a plurality of peptides each including no more than 4 amino acids, wherein at least one of the 4 amino acids is an aromatic amino acid; and (b) using the at least one nanostructure for grabbing and/or manipulating the nanoscale objects.

According to further features in preferred embodiments of the invention described below, the at least one nanostructure are a first tubular nanostructure and a second tubular nanostructure, the first and the second tubular nanostructures being capable of at least a constrained motion.

According to still further features in the described preferred embodiments the method further comprises generating electrostatic force between the first and the second tubular nanostructures, thereby closing or opening the first and the second tubular nanostructures on the nanoscale object.

According to still a further aspect of the present invention there is provided a method of transferring heat, the method comprising: (a) providing a channel filled with a nanofluid comprising nanostructures suspended in a fluid, wherein at least a portion of the nanostructures is composed of a plurality of peptides, each including no more than 4 amino acids, wherein at least one of the 4 amino acids is an aromatic amino acid; and (b) placing the channel in proximity to a heat source such that the nanofluid transfers heat from a first end of the channel to a second end thereof.

According to further features in preferred embodiments of the invention described below, the channel is selected from the group consisting of a microchannel and a nanochannel.

According to still further features in the described preferred embodiments the method further comprises generating locomotion of the nanofluid within the channel.

According to still further features in the described preferred embodiments the nanostructures are selected from the group consisting of spherical nanostructures and tubular nanostructures.

According to still further features in the described preferred embodiments the nanostructure is coated by a conductive material.

According to still a further aspect of the present invention there is provided a composition comprising: (i) a tubular, spherical or planar nanostructure being composed of a plurality of peptides, wherein each of the plurality of peptides includes no more than 4 amino acids and whereas at least one of the 4 amino acids is an aromatic amino acid; and (ii) an agent being attached to the tubular, spherical or planar nanostructure.

According to further features in preferred embodiments of the invention described below, the agent is a drug.

According to still further features in the described preferred embodiments the agent is a nucleic acid molecule.

According to still further features in the described preferred embodiments the agent is a polypeptide.

According to still further features in the described preferred embodiments the agent is capable of being slowly released from the nanostructure.

According to still further features in the described preferred embodiments the nanostructure does not exceed 500 nm in diameter.

According to still further features in the described preferred embodiments the tubular nanostructure is at least 1 nm in length.

According to still a further aspect of the present invention there is provided a composition for modulated delivery of a chemical to a predetermined location, the composition comprising: a plurality of nanoshells, the nanoshells having a nanostructure core and a conductive shell and being capable of converting incident radiation into heat energy, the nanostructure core is composed of a plurality of peptides, each including no more than 4 amino acids, wherein at least one of the 4 amino acids is an aromatic amino acid; and a medium comprising the chemical and a thermally responsive material in thermal contact with the nanoshells.

According to still a further aspect of the present invention there is provided a method for inducing localized hyperthermia in a cell or tissue of an individual, the method comprising: delivering a plurality of nanoshells, each having a nanostructure core and a conductive shell and being capable of converting incident radiation into heat energy, the nanostructure core is composed of a plurality of peptides, each including no more than 4 amino acids, wherein at least one of the 4 amino acids is an aromatic amino acid; and exposing the nanoshells to the incident radiation to thereby convert the incident radiation into the heat energy.

According to further features in preferred embodiments of the invention described below, the conductive shell is a metal shell.

According to further features in preferred embodiments of the invention described below, the incident radiation is selected from the group consisting of an electromagnetic wave, an electric field, a magnetic field and an ultrasound wave.

According to still further features in the described preferred embodiments the nanoshells comprise an affinity component having affinity to the cell or the tissue.

According to still further features in the described preferred embodiments the affinity component comprises a moiety selected from the group consisting of an antibody, an antigen, a ligand and a substrate.

According to still further features in the described preferred embodiments each of the 4 amino acids is independently selected from the group of naturally occurring amino acids, synthetic amino acids, β-amino acids, Peptide Nucleic Acid (PNA) and combinations thereof.

According to still further features in the described preferred embodiments at least one of the 4 amino acids is a D-amino acid.

According to still further features in the described preferred embodiments at least one of the 4 amino acids is an L-amino acid.

According to still further features in the described preferred embodiments at least one of the peptide nanostructures comprises at least two aromatic moieties.

According to still further features in the described preferred embodiments at least one of the peptide nanostructures is a homodipeptide. According to still further features in the described preferred embodiments each of the amino acids is the homodipeptide comprises an aromatic moiety, such as, but not limited to, substituted naphthalenyl, unsubstituted naphthalenyl, substituted phenyl or unsubstituted phenyl.

According to still further features in the described preferred embodiments the substituted phenyl is selected from the group consisting of pentafluoro phenyl, iodophenyl, biphenyl and nitrophenyl.

Thus, representative examples of the amino acids in the homopeptide include, without limitation, naphthylalanine, p-nitro-phenylalanine, iodo-phenylalanine and fluoro-phenylalanine.

According to still further features in the described preferred embodiments the homodipeptide is selected from the group consisting of naphthylalanine-naphthylalanine dipeptide (SEQ ID NO: 9), (pentafluoro-phenylalanine)-(pentafluoro-phenylalanine) dipeptide (SEQ ID NO: 10), (iodo-phenylalanine)-(iodo-phenylalanine) dipeptide (SEQ ID NO: 11), (4-phenyl phenylalanine)-(4-phenyl phenylalanine) (SEQ ID NO: 12) dipeptide and (p-nitro-phenylalanine)-(p-nitro-phenylalanine) dipeptide (SEQ ID NO: 13).

According to still further features in the described preferred embodiments the nanostructure is stable at a temperature range of 4-400° C.

According to still further features in the described preferred embodiments the nanostructure is stable in an acidic environment.

According to still further features in the described preferred embodiments the nanostructure is stable in a basic environment.

According to still further features in the described preferred embodiments the nanostructure is coated by a conductive material.

According to still further features in the described preferred embodiments the nanostructure does not exceed 500 nm in diameter.

According to still further features in the described preferred embodiments the nanostructure is at least 1 nm in length.

According to still further features in the described preferred embodiments the nanostructure is biodegradable.

According to still a further aspect of the present invention there is provided a nanostructure composed of a plurality of polyaromatic peptides.

According to still further features in the described preferred embodiments the polyaromatic peptides are selected from the group consisting of polyphenylalanine peptides, polytryptophane peptides, polytyrosine peptides, non-natural derivatives thereof and combinations thereof.

According to still further features in the described preferred embodiments the polyaromatic peptides are at least 30 amino acids in length.

The present invention successfully addresses the shortcomings of the presently known configurations by providing a novel peptide nanostructure which can be used in numerous mechanical, electronically, chemical, optical and biotechnological applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration of a device for obtaining information from a nanoscale environment, according to a preferred embodiment of the present invention.

FIG. 2a is a schematic illustration of a field emitter device, according to a preferred embodiment of the present invention.

FIG. 2b is a schematic illustration of a matrix of row and column electrodes, according to a preferred embodiment of the present invention.

FIG. 3 is a schematic illustration of an apparatus for electron emission lithography, according to a preferred embodiment of the present invention.

Figure 4A:
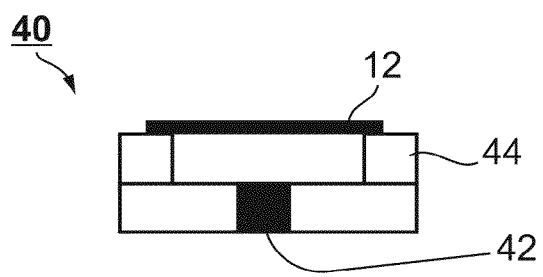
Figure 4B:
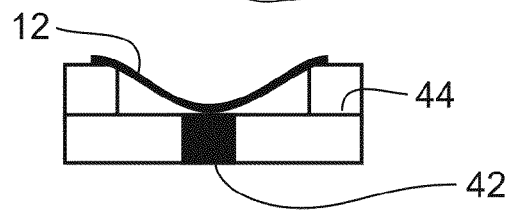

FIGS. 4a-b are schematic illustration of a memory cell, according to a preferred embodiment of the present invention.

Figure 5A:
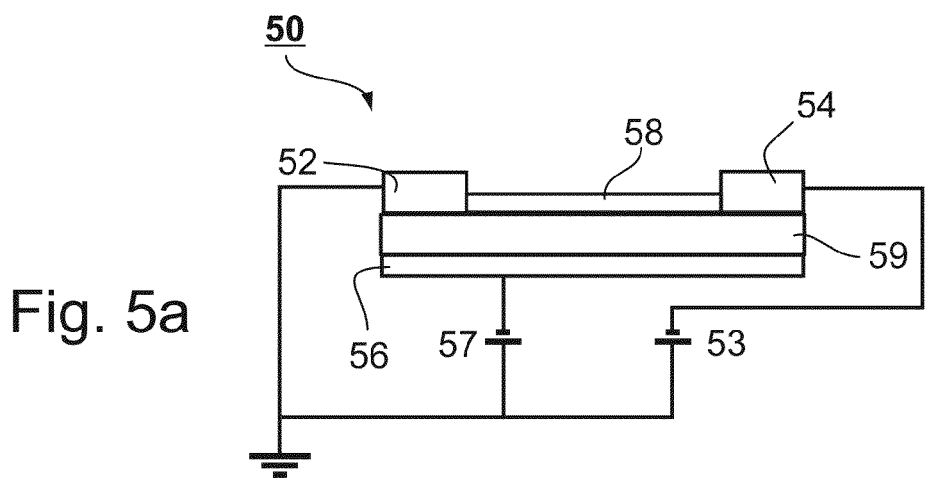

FIG. 5a is a schematic illustration of an electronic device for switching, inverting or amplifying, according to a preferred embodiment of the present invention.

Figure 5B:
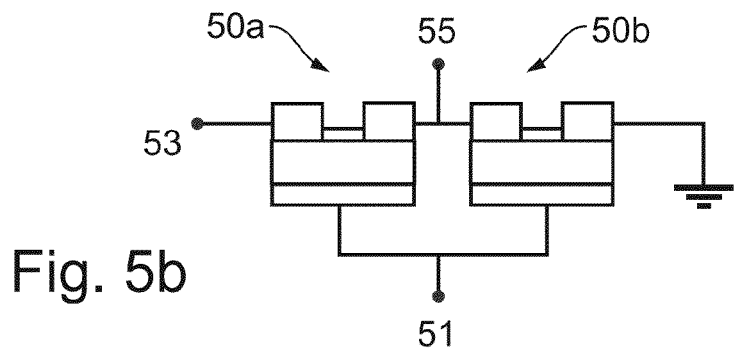

FIG. 5b is a schematic illustration of an inverter, which is formed from two devices, each similar to the device of FIG. 5a, according to a preferred embodiment of the present invention.

Figure 6:
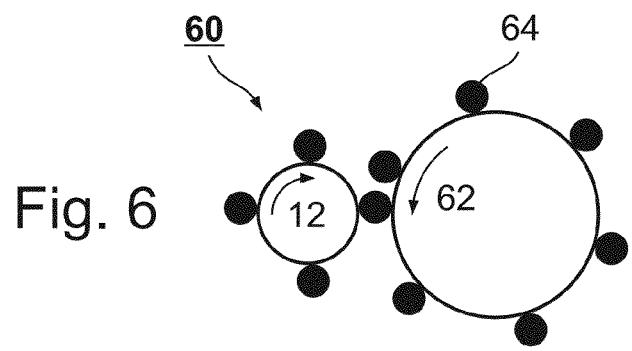

FIG. 6 is a schematic illustration of a mechanical transmission device, according to a preferred embodiment of the present invention.

Figure 7:
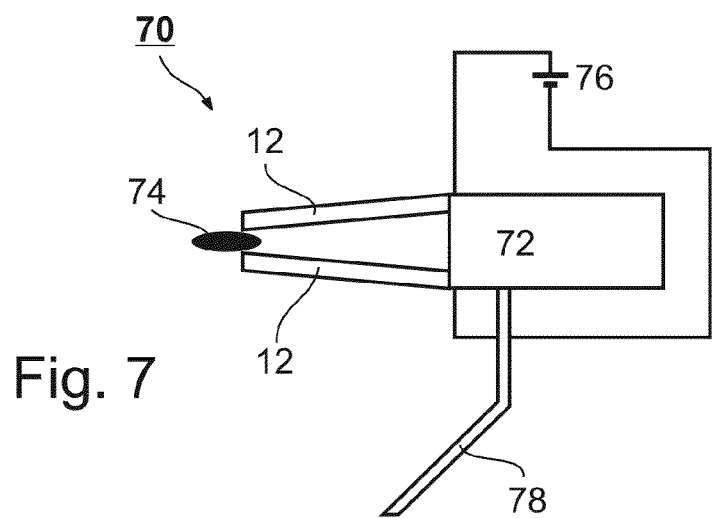

FIG. 7 is a schematic illustration of a nanoscale mechanical device for griping and/or manipulating objects of nanometric size, according to a preferred embodiment of the present invention.

Figure 8:
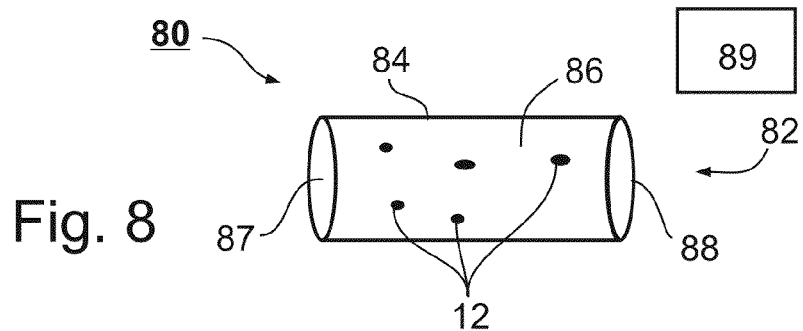

FIG. 8 is a schematic illustration of a heat transfer device, according to a preferred embodiment of the present invention.

Figure 9A:
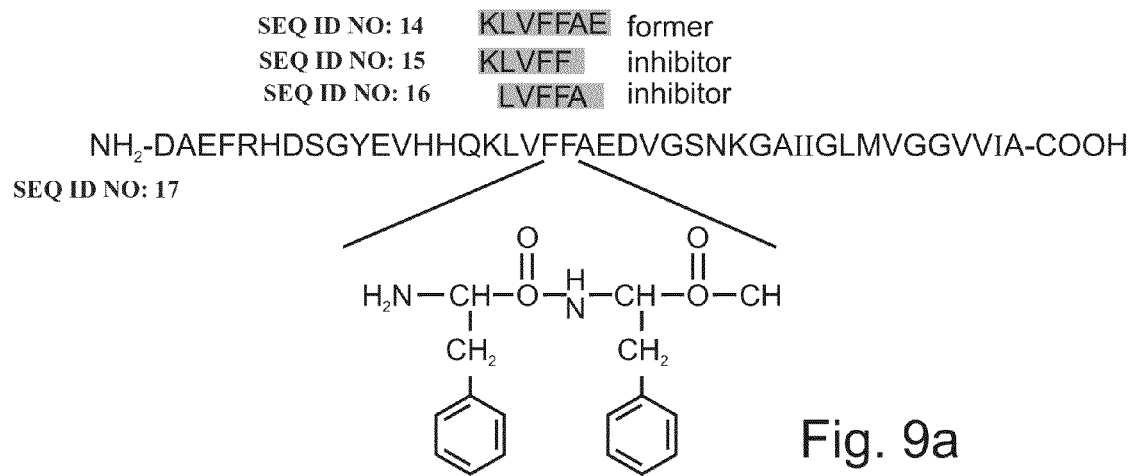
Figure 9B:
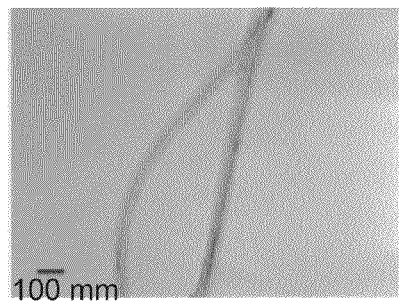
Figure 9C:
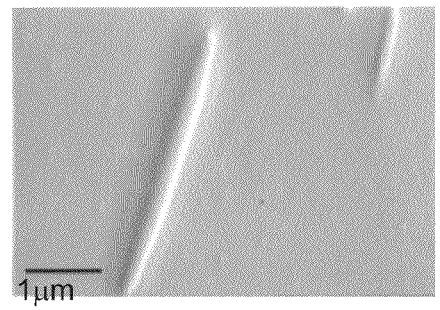
Figure 9D:
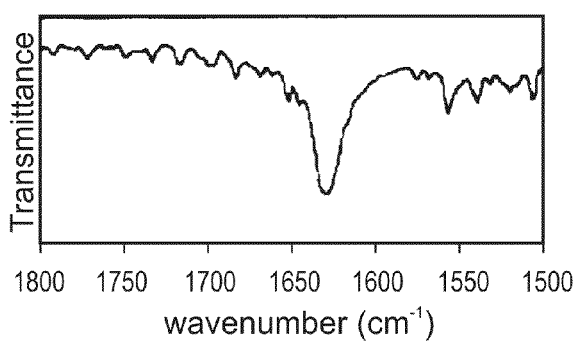
Figure 9E:

FIGS. 9a-e are photomicrographs depicting the ability of diphenylalanine peptides to form nanotubes. FIG. 9a is a schematic illustration showing the central aromatic core structure of the β-amyloid polypeptide which is involved in the formation of amyloid fibrils. FIG. 9b is a photomicrograph showing the assembly of diphenylalanine peptides into nanostructures as determined by Transmission Electron Microscopy. FIG. 9c is a photomicrograph showing a single nanotubes as visualized by electron microscopy. FIG. 9d is a graph showing Fourier-transformed infrared spectral analysis of the nanostructures. FIG. 9e is a photomicrograph showing green-gold birefringence of Congo-red stained structures visualized between cross polarizers.

FIGS. 10a-b are photomicrographs depicting self-assembly of well-ordered and elongated peptide nanotubes by a molecular recognition motif derived from the β-amyloid polypeptide. FIG. 10a is a TEM image of the negatively-stained nanotubes formed by the diphenylalanine peptide. FIG. 10b is an HR-TEM image of negatively-stained peptide nanotubes.

FIGS. 11a-b are SEM images depicting the tubular nanoparticles. FIG. 11a is a Low magnification SEM image of a field of discrete nanotubes existed as individual entities. The scale bar represents 1 μm. FIG. 11b is a high magnification SEM image of an individual nanotube. The scale bar represents 200 nm.

FIG. 11c is a graph showing a statistical distribution of the size of the nanotubes.

Figure 12A:
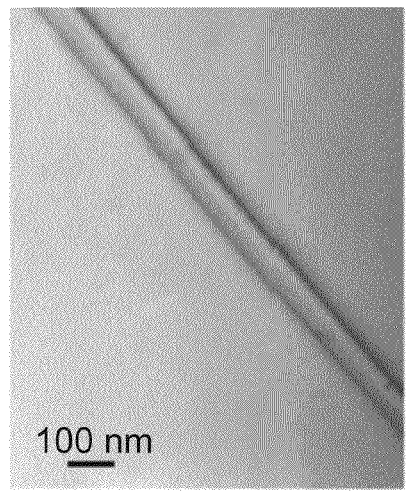
Figure 12B:
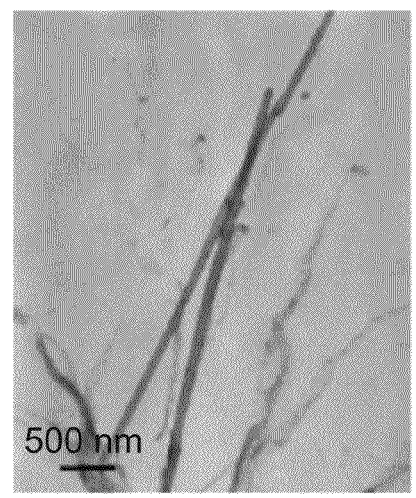

FIGS. 12a-b are photomicrographs depicting the formation of peptide nanotubes by different aromatic peptide. FIG. 12a is a TEM image of stable nanotubes formed by the self-assembly of D-amino acid building block analogue. FIG. 12b is a TEM image of a tubular structure formed by the NH2-Phe-Trp-COOH dipeptide (SEQ ID NO: 5). Note, the amorphous aggregates at the background of the image.

Figure 13A:
Figure 13B:
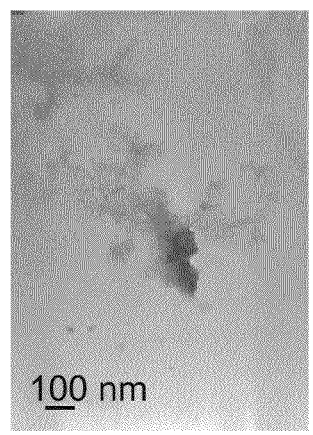
Figure 13C:
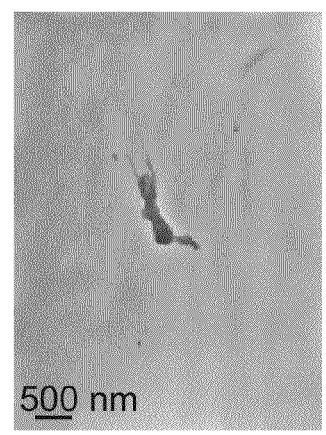

FIGS. 13a-c are photomicrographs showing the ability of aromatic peptides to form nanotubes as determined by TEM analysis and negative staining. All peptides were dissolved in HFIP and added to double distilled water at a final concentration of 2 mg/ml. Then a 10 μl aliquot of 1 day-aged solution of peptide was placed on 400 mesh copper grid. Following 1 minute, excess fluid was removed. In negative staining experiments, the grid was stained with 2% uranyl acetate in water and after two minutes excess fluid was removed from the grid. FIG. 13a—NH2-Trp-Trp-COOH (SEQ ID NO: 2); FIG. 13b—NH2-Trp-Tyr-COOH (SEQ ID NO: 3); FIG. 13c—NH2-Trp-Phe-COOH (SEQ ID NO: 4).

Figure 14:
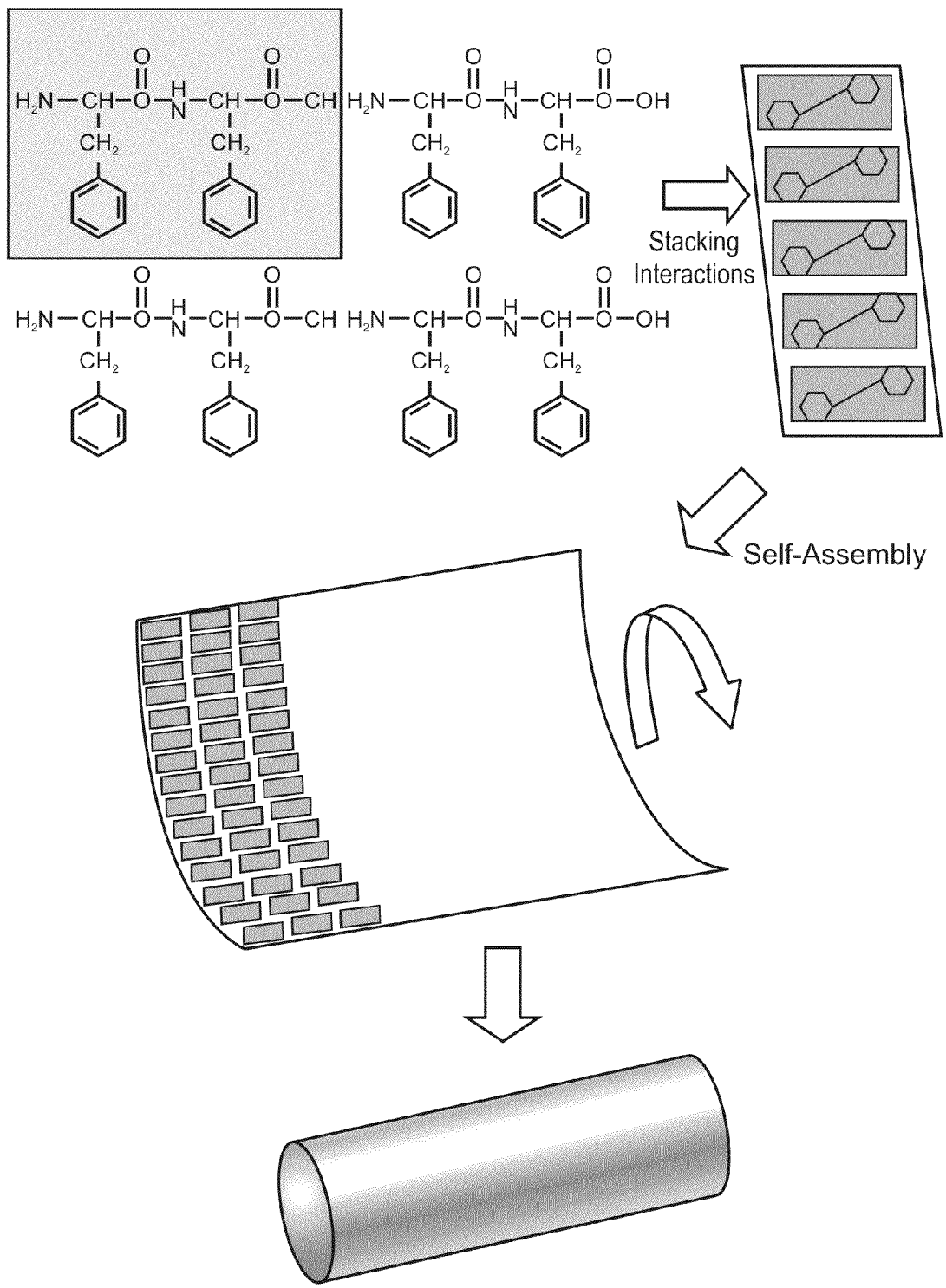

FIG. 14 is a schematic illustration of a proposed assembly mechanism for the formation of peptide nanotubes. A stacking interaction between aromatic moieties of the peptides is suggested to provide energetic contribution as well as order and directionality for the initial interaction. The spectroscopic evidence of β-sheet conformation of the single amide bond is reflected by an extension of the amino-acids residues to opposite sides and the formation of an extended pleated sheet that is stabilize by hydrogen bonds and aromatic stacking interactions. The formation of the tubular structures may occur by a closure of the extended sheet as previously suggested [Matsui and Gologan (2000) J. Phys. Chem. B 104: 3383].

FIGS. 15a-d depict self-assembly of spherical nanometric structures by the aromatic peptide, diphenylglycine. FIG. 15a is a schematic illustration showing the diphenylalanine motif, the central core of the β-amyloid polypeptide, which forms discrete well-ordered peptide nanotubes. FIG. 15b is a schematic illustration showing the simplest aromatic dipeptide, the diphenylglycine peptide. FIG. 15c is a photomicrograph depicting Low magnification transmission electron microscopy (TEM) image of negatively stained nanospheres formed by the diphenyglycine peptide. FIG. 15d is a photomicrograph depicting high magnification TEM image of the negatively stained nanosphere.

Figure 16A:
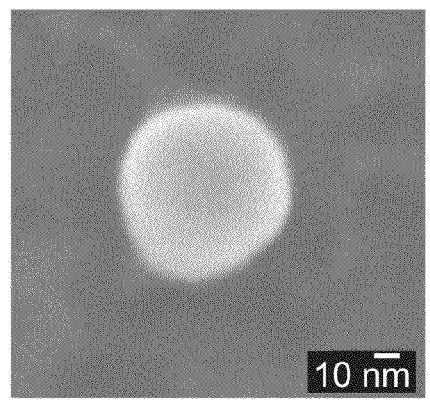
Figure 16B:
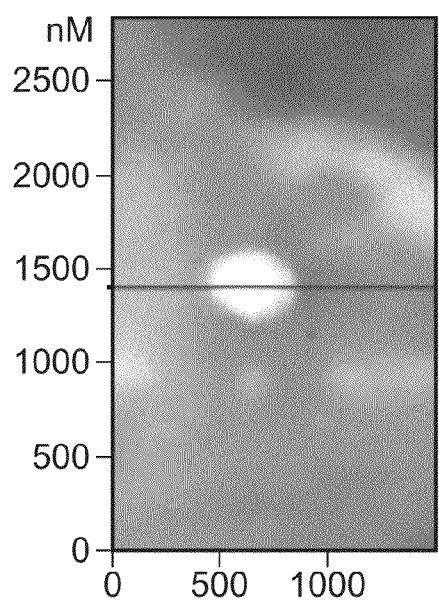
Figure 16B:
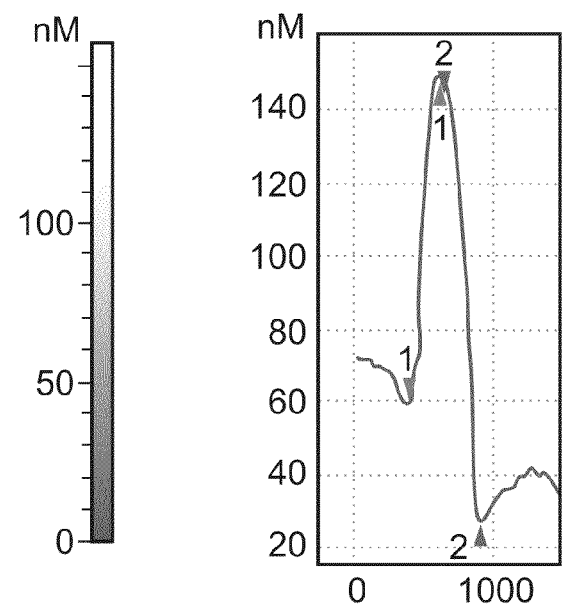
Figure 16C:
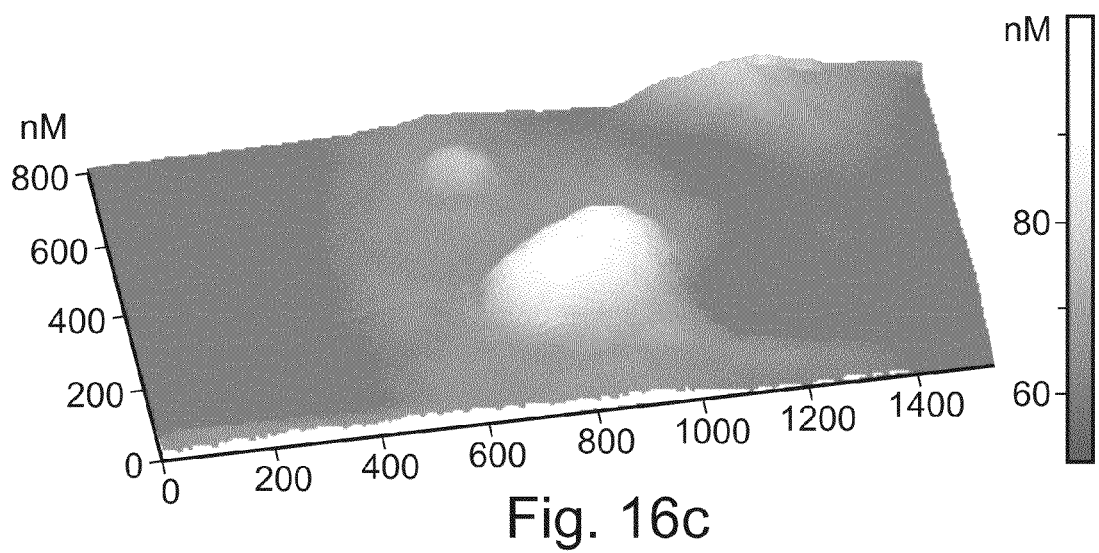

FIGS. 16a-c are photomicrographs showing structural properties of self-assembled nanospheres. FIG. 16a shows high magnification (×400,000) cold field emission gun (CFEG) high-resolution scanning electron microscope (HR-SEM) image of the nanospheres formed by the diphenygly-SEM) peptide. FIG. 16b shows the nanospheres height as analyzed by atomic force microscopy (AFM) topography. FIG. 16c is a three-dimensional AFM topography image of the nanospheres.

FIGS. 17a-b are photomicrographs depicting the stability of the nanostructures at extreme chemical conditions, as observed by TEM. Self-assembled nanospheres were incubated in the presence of strong acid or base FIG. 17a shows the nanospheres following 5 hours of incubation in the presence of 10% TFA. FIG. 17b shows the nanospheres following 5 hours of incubation in the presence of 1M NaOH.

Figure 18A:
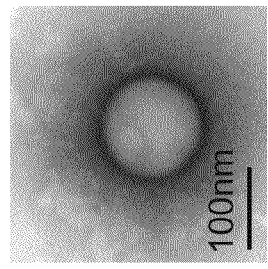
Figure 18B:
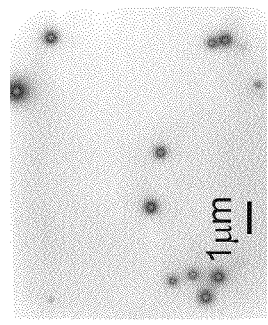
Figure 18C:
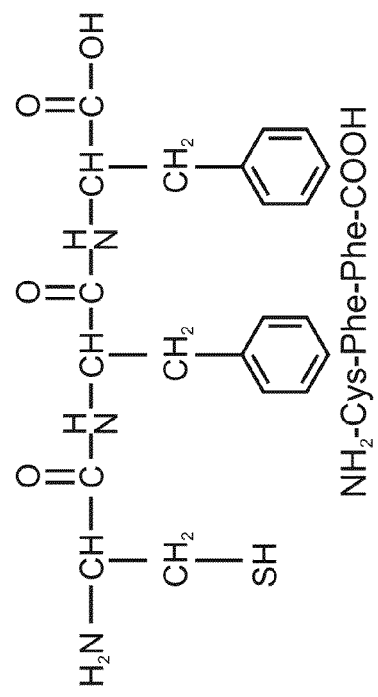
Figure 18D:
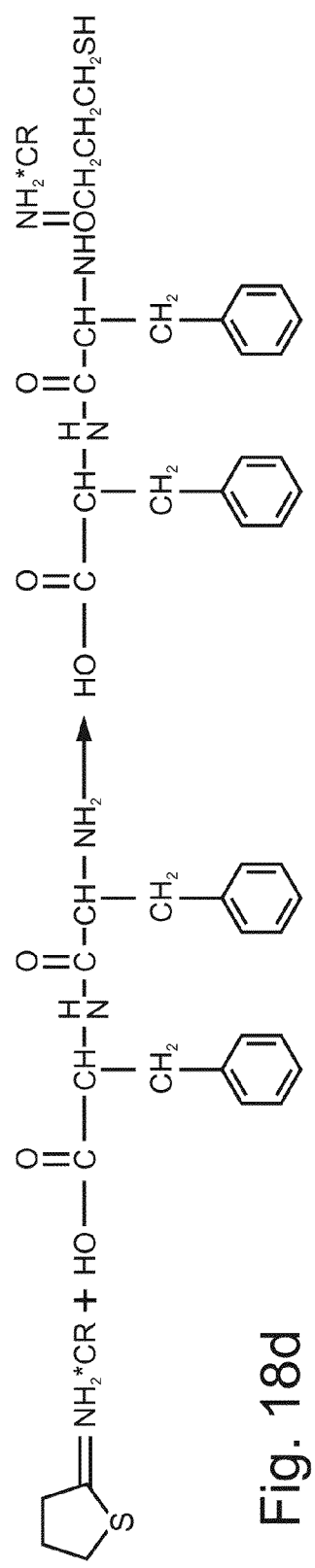
Figure 18D:
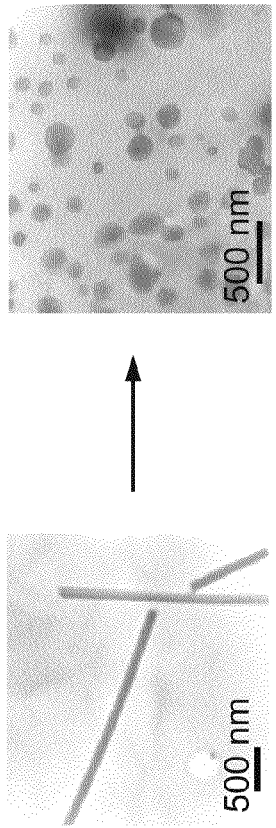

FIGS. 18a-d are photomicrographs showing the formation of nanospheres by peptides which include a thiol group. FIG. 18a is a schematic presentation of the Cys-Phe-Phe (CFF) tripeptide. FIG. 18b is a photomicrograph showing low magnification TEM microphage of the nanospheres formed by the CFF peptide. FIG. 18c is a photomicrograph showing high magnification TEM microphage of the nanospheres formed by the CFF peptide. FIG. 18d is a schematic presentation of the chemical reaction that modifies an amine to a thiol in the context of the diphenylalanine peptide. FIG. 18e is a photomicrograph showing low magnification TEM microphage of the nanotubes formed by the FF peptide. FIG. 18b is a photomicrograph showing low magnification TEM microphage of the nanospheres formed by FF peptide that self-assembled in the presence of 2-iminothiolane.

Figure 19A:
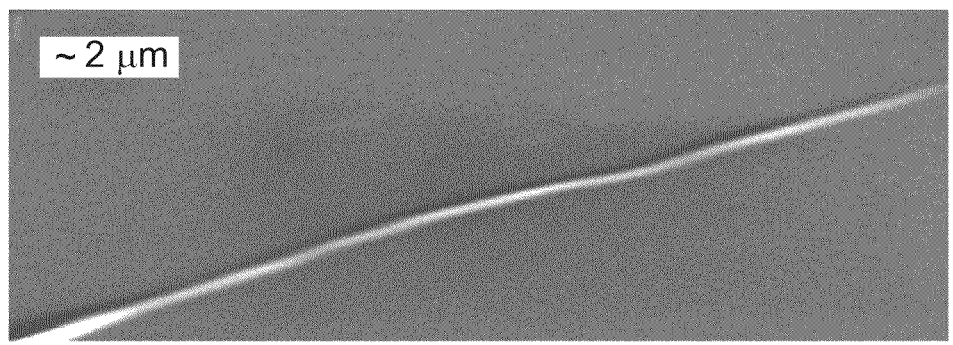
Figure 19B:
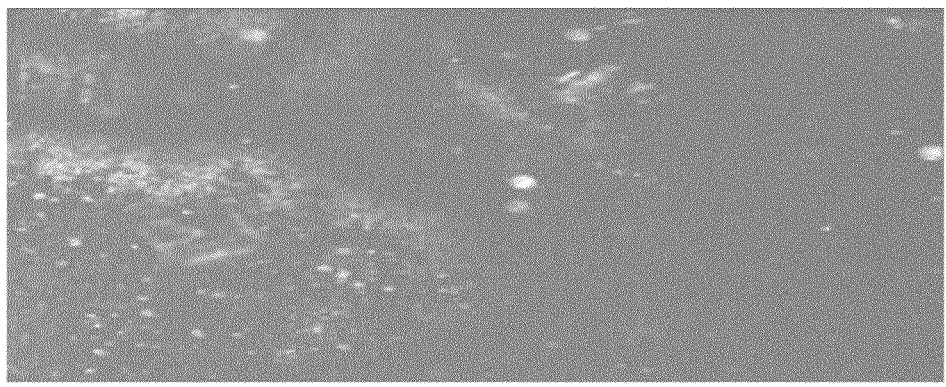
Figure 19C:
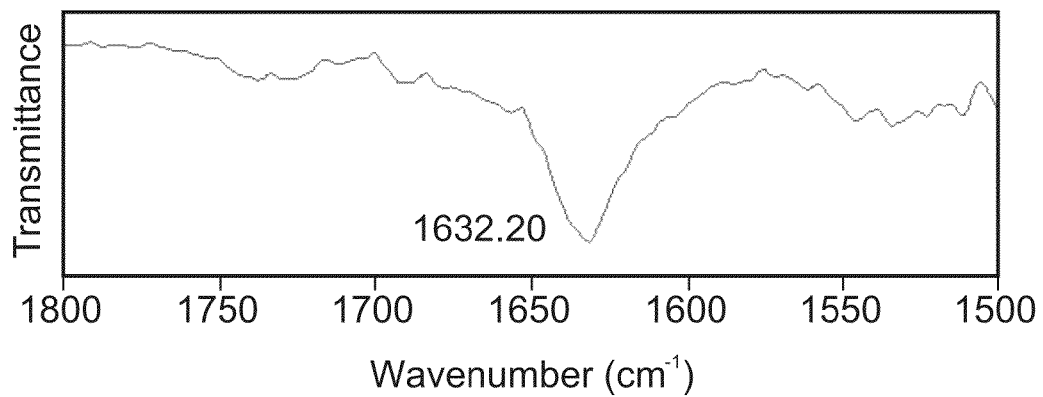

FIGS. 19a-c show the self-assembly of tubular nanometric structures by polyphenylalanine peptides. FIG. 19a is a scanning electron microscopy (SEM) image showing the nanotubes formed by the polyphenylalanine peptide. FIG. 19b is a photomicrograph showing Congo Red staining of 1 day aged solution of polyphenylalanine peptide nanotubes. FIG. 19c is a graph showing the secondary structure of polyphenylalanine nanotubes as determined by Fourier transform infrared spectroscopy.

Figure 20:
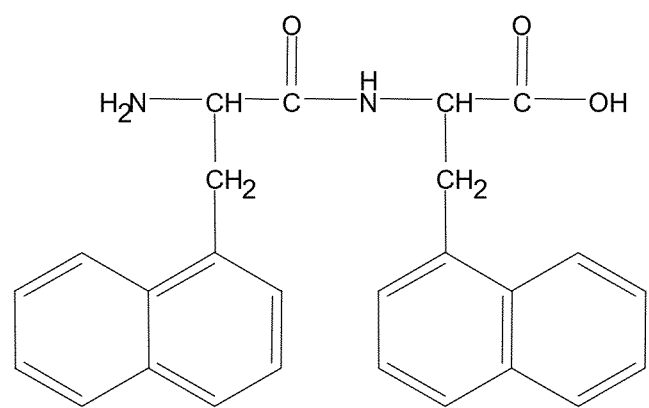

FIG. 20 is a schematic illustration of a chemical structure of a naphthylalanine-naphthylalanine (Nal-Nal) dipeptide.

Figure 21:
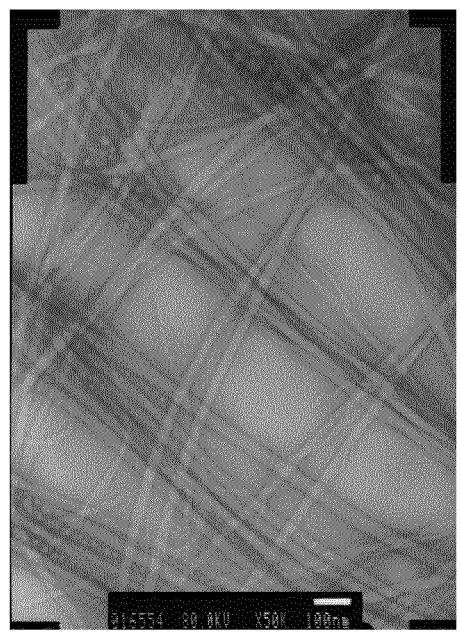

FIG. 21 is an electron microscope image of Nal-Nal tubular nanostructures.

Figure 22A:
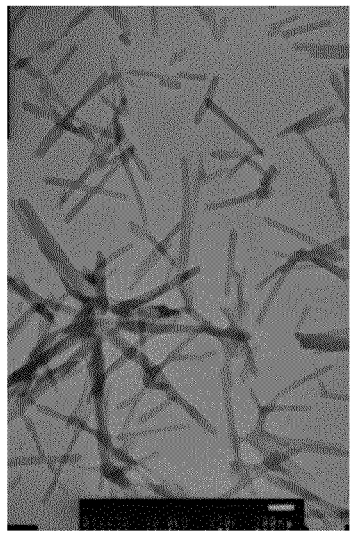
Figure 22B:
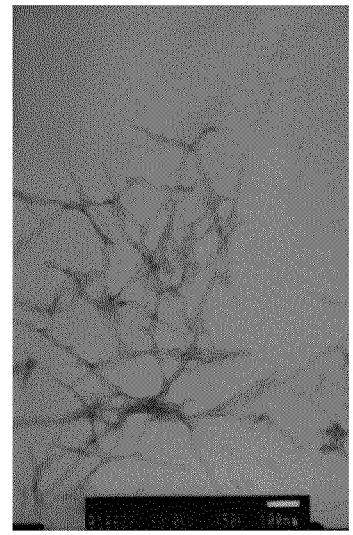
Figure 22C:
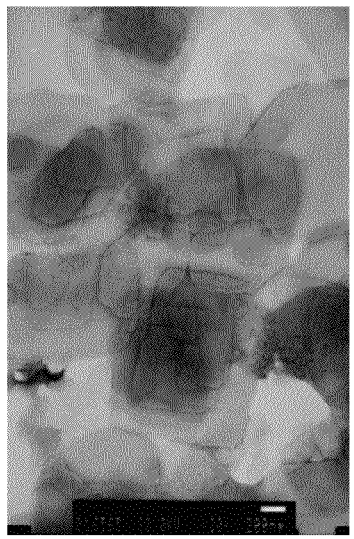
Figure 22D:
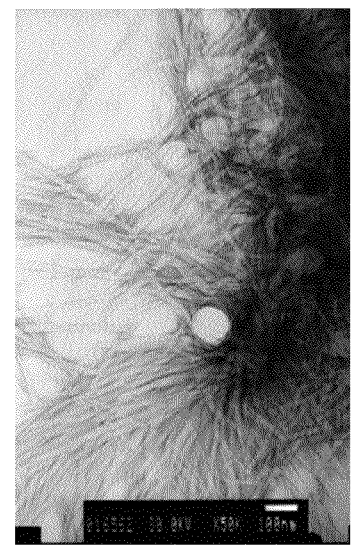

FIGS. 22a-d are electron microscope images of tubular and planar nanostructures assembled from the following aromatic-homodipeptides: (pentafluoro-phenylalanine)-(pentafluoro-phenylalanine) (FIG. 22A), (iodo-phenylalanine)-(iodo-phenylalanine) (FIG. 22B), (4-phenyl phenylalanine)-(4-phenyl phenylalanine) (FIG. 22C), and (p-nitro-phenylalanine)-(p-nitro-phenylalanine) (FIG. 22D).

DESCRIPTION OF THE PREFERRED EMBODIMENTS

The present invention is of a peptide nanostructures and methods of generating same, which can be used in numerous applications. Specifically, the present invention can be used in numerous applications, such as, but not limited to, transistors, field emitters, display devices, memory chips, cooling systems and nano-mechanical devices.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Self-assembled nanostructures allow controlled fabrication of novel nanoscopic materials and devices. Nanotubular structures are particularly important structural elements as they may serve in numerous applications, for example, as nanowires and nanoscaffolds. Most widely used nanotubes are made of carbon or peptide assemblers (i.e., building blocks). While carbon nanotubes, suffer from major structural defects including branching and bending resulting in spatial structures with unpredictable electronic, molecular and structural properties, peptide nanotubes such as those composed of surfactant like peptides and cyclic D-, L-peptide subunits are formed either as crystals, networks, or bundles of nanostructures.

While reducing the present invention to practice, the present inventor uncovered that aromatic peptides (e.g., diphenylalanine) are capable of forming tubular, spherical and planar nanostructures, which can be used in numerous mechanical, electrical, chemical, optical and biotechnological systems.

It will be appreciated that the term nanotubes was previously attributed to the hollow nanometric channels, which are formed within the macroscopic crystal structure of diphenylalanine peptides. However, these entities are not the individual nanostructures formed by the present invention, but rather are macrioscopic bundles, which cannot be used as nanotubes [Gorbitz (2001) Chemistry 38:6791].

This discrepancy in results can be explained by the different conditions which were used to assemble the structures. While Gorbitz allowed crystallization by evaporation of an aqueous peptide solution in high temperature (i.e., 80° C.), the present inventor allowed self-assembly in an aqueous solution under mild-conditions (see Example 1 of the Examples section which follows).

Thus, according to one aspect of the present invention, there is provided a tubular, spherical or planar nanostructure.

The nanostructure of this aspect of the present invention is composed of a plurality of peptides, each peptide including no more than 4 amino acids of which at least one is an aromatic amino acid.

As used herein the phrase "tubular, spherical or planar nanostructure" refers to a planar (e.g., disk-shape), spherical elongated tubular or conical structure having a diameter or a cross-section of less than 1 μm (preferably less than 500 nm, more preferably less than about 50 nm, even more preferably less than about 5 nm). The length of the tubular nanostructure of the present invention is preferably at least 1 μm, more preferably at least 10 nm, even more preferably at least 100 nm and even more preferably at least 500 nm. It will be appreciated, though, that the tubular structure of the present invention can be of infinite length (i.e., macroscopic fibrous structures) and as such can be used in the fabrication of hyper-strong materials.

The nanostructure of the present invention is preferably hollow, conductive or semi-conductive.

According to a preferred embodiment of this aspect of the present invention the peptide is a dipeptide or a tripeptide such as set forth in SEQ ID NO: 1, 5, 6, 7 or 8 (see the Examples section which follows). Depending on the rigidity of the molecular structure of the peptide used, tubular, spherical or planar nanostructures are formed. Thus, for example a plurality of diphenylglycine peptides which offer similar molecular properties as diphenylalenine peptides albeit with a lower degree of rotational freedom around the additional C—C bond and a higher steric hindrance will self-assemble into nano spheres, while a plurality of diphenylalenine peptides will self-assemble into nanotubes.

The present invention also envisages nanostructures which are composed of a plurality of polyaromatic peptides being longer than the above described (e.g., 50-136 amino acids).

As used herein the phrase "polyaromatic peptides" refers to peptides which include at least 80%, at least 85% at least 90%, at least 95% or more, say 100% aromatic amino acid residues. These peptides can be homogenic (e.g., polyphenylalanine, see Example 3 of the Examples section which follows) or heterogenic of at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 120, at least 125, at least 130, at least 135, at least 140, at least 145, at least 150, at least 155, at least 160, at least 170, at least 190, at least 200, at least 300, at least 500 amino acids.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N (CH3)—CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylalanine (Nal), ring-methylated derivatives of Phe, halogenated derivatives of Phe or O-methyl-Tyr, and β amino-acids.

In addition to the above, the peptides of the present invention may also include one or more modified amino acids (e.g., thiolated amino acids, see Example 2 of the Examples section, or biotinylated amino acids) or one or more non-amino acid monomers (e.g. fatty acids, complex carbohydrates etc). Also contemplated are homodipeptides, and more preferably aromatic homodipeptides in which each of the amino acids comprises an aromatic moiety, such as, but not limited to, substituted or unsubstituted naphthalenyl and substituted or unsubstituted phenyl. The aromatic moiety can alternatively be substituted or unsubstituted heteroaryl such as, for example, indole, thiophene, imidazole, oxazole, thiazole, pyrazole, pyridine, pyrimidine, quinoline, isoquinoline, quinazoline, quinoxaline and purine.

When substituted, the phenyl, naphthalenyl or any other aromatic moiety includes one or more substituents such as, but not limited to, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

As used herein, the term "alkyl" refers to a saturated aliphatic hydrocarbon including straight chain and branched chain groups. Preferably, the alkyl group has 1 to 20 carbon atoms. The alkyl group may be substituted or unsubstituted. When substituted, the substituent group can be, for example, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano and amine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, trihaloalkyl, alkenyl, alkynyl, cycloalkyl, aryl, heteroaryl, heteroalicyclic, halo, nitro, azo, hydroxy, alkoxy, thiohydroxy, thioalkoxy, cyano, and amine. Representative examples are piperidine, piperazine, tetrahydro furane, tetrahydropyrane, morpholino and the like.

A "hydroxy" group refers to an —OH group.

An "azide" group refers to a —N═N≡N group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to an —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "halo" group refers to fluorine, chlorine, bromine or iodine.

A "trihaloalkyl" group refers to an alkyl substituted by three halo groups, as defined herein. A representative example is trihalomethyl.

An "amino" group refers to an —NR'R" group where R' and R" are hydrogen, alkyl, cycloalkyl or aryl.

A "nitro" group refers to an —NO$_2$ group.

A "cyano" group refers to a —C≡N group.

Representative examples of such homodipeptides include, without limitation, a naphthylalanine-naphthylalanine (Nal-Nal) dipeptides, (pentafluoro-phenylalanine)-(pentafluoro-phenylalanine), (iodo-phenylalanine)-(iodo-phenylalanine), (4-phenyl phenylalanine)-(4-phenyl phenylalanine) and (p-nitro-phenylalanine)-(p-nitro-phenylalanine) (see Example 4-5 and FIGS. 20-22).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |

TABLE 2-continued

| Non-conventional amino acid | Code | Non-conventional amino acid | Code |
|---|---|---|---|
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The nanostructures of the present invention are preferably generated by allowing a highly concentrated aqueous solution of the peptides of the present invention to self-assemble under mild conditions as detailed in Examples 1 and 2 of the Examples section which follows.

The resulting nanostructures are preferably stable under acidic and/or basic pH conditions, a wide range of temperatures (e.g., 4-400° C., more preferably, 4-200° C.) and/or proteolytic conditions (i.e., proteinase K).

Depending on the number and type of amino acids used, the nanostructure can be insulators, conductors or semiconductors. The nanostructure of the present invention can also be utilized as carriers onto which atoms of different materials (e.g., conductive materials, chemical or biological agents, etc.) may be incorporated.

A detailed description of the nanostructure generated according to the teachings of the present invention follows below, starting first with a description of the applications of such nano structures and the advantages offered thereby.

The nanostructure of the present invention has numerous potential applications. Having a substantially high aspect ratio, the nanostructure of the present invention is an ideal candidate for use in probing application. For example, a nanostructure having a tip diameter of about 10 nm and a length of several micrometers can be used as the tip of an atomic force microscope to probe deep crevices found on integrated circuits, biological molecules or any other nanoscale environment.

Additionally, the nanostructure of the present invention has exceptional material properties. More specifically, due to multiple cooperative forces (hydrogen bonding and hydrophobic packing), the nanostructure is highly robust under extreme pH and temperatures. When another material (e.g., a polymer or a ceramic material) is reinforced with the nanostructure of the present invention, the resulting composition is characterized by a mechanical strength of one or more order of magnitude above the strength of the host material. Such a strong composite material is well suited for many applications such as, but not limited to, in the defense, aerospace and automobile industries.

An additional potential application of the nanostructure of the present invention is in the field of micro- and nanoelectronic systems. The nanostructure can be combined with silicon chips so as to restrict motion of electrons or holes within a nanoscale region thereby to provide the system with special electric, optical and/or chemical characteristics. For example, the use of nanostructure as gates in an electronic device allows operation at low gate voltage and enables the switching of several individual devices on the same substrate.

As mentioned hereinabove, the nanostructures of the present invention can be hollow. Being both of nanometer scale and hollow, the nanostructures can serve for heat conduction, e.g., by mixing the nanostructures with a fluid (e.g., a cooling liquid).

Still another potential applications of the nanostructure of the present invention is related to enhancement of electromagnetic fields near ultra small metal objects. The physical process of strong field enhancement very close to metal nanoparticles is a well known phenomenon and has been described in detail in the literature. To this end, see, for example, R. H. Doremus and P. Rao, *J. Mater. Res.,* 11, 2834 (1996); M. Quinten, *Appl. Phys. B* 73, 245 (2001) and R. D. Averitt, S. L. Westcott and N. J. Halas, *J. Opt. Soc. Am. B* 16, 1824 (1999), the contents of which are hereby incorporated by reference. In metal nanoparticles, resonant collective oscillations of conduction electrons, also known as particle plasmons, are excited by an optical field. The resonance frequency of a particle plasmons is determined mainly by the dielectric function of the metal, the surrounding medium and by the shape of the particle. Resonance leads to a narrow spectrally selective absorption and an enhancement of the local field confined on and close to the surface of the metal particle. The spectral width of absorption and near-field enhancement depends on the decay time of the particle plasmons. A significant enhancement of the effect of optical field increment may be achieved, by coating the nanostructures of the present invention by a conducting shall layer. Nanoparticles having such structure are called nanoshells.

The process of coating nanostructures having a dielectric core and to form a conducting shell, is known in the art and is described in, for example, WO 01/06257 and WO 02/28552, the contents of which are hereby incorporated by reference.

Following are representative examples of applications in which the nanostructure of the present invention is preferably incorporated.

Hence, further in accordance with the present invention there is provided a device for obtaining information from a nanoscale environment. Broadly speaking, this device is capable of serving as an interface between macroscopic systems and individual objects having nanometer dimensions. The device according to this aspect of the present invention may comprise one or more nanostructures, which facilitate information exchange between the macroscopic system and the nanoscale environment. Individual nanostructures or bundles of nanostructures can be recovered from peptides, as further detailed hereinabove, in accordance with the present invention. Assemblies of nanostructures can be fabricated, for example, by self-assembly of groups of nanostructures, as further detailed and exemplified in the Examples section that follows.

Figure 1:
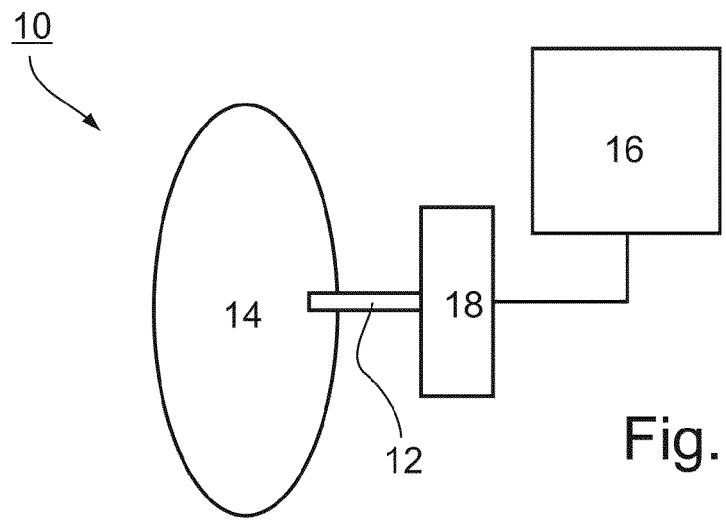

Referring now to the drawings, FIG. 1 is a schematic illustration of the device described above, which is referred to herein as device 10. In its most basic form, device 10 comprises a nanostructure 12 and a detection system 16. As stated, nanostructure 12 preferably comprises a plurality of peptides, each having no more than 4 amino acids.

Nanostructure 12 serves for collecting signals from a nanoscale environment 14. Any type of signals can be collected by nanostructure 12 including, without limitation, mechanical, optical, electrical, magnetic and chemical signals. Detection system 16 serves for interfacing with nanostructure 12 and receiving the signals collected thereby. Hence, by collecting signals using nanostructure 12 and detecting the signals using system 16, device 10 is capable of sensing, measuring and analyzing nanoscale environment 14.

According to a preferred embodiment of the present invention device 10 may further comprise a supporting element 18 onto which nanostructure 12 is mounted. Nanostructure 12 is connected to supporting element 18 at one end, with the other end being free and, due to its nanometric dimension, capable of coming into direct contact or near proximity to nanoscale environment 14. Preferably, supporting element 18 can physically scan nanoscale environment 14 to thereby allow nanostructure 12 to collect signals from, or deliver signals to a plurality of locations of nanoscale environment 14. The "sensing end" of nanostructure 12 interacts with objects being sensed, measured or analyzed by means which are (either individually or in combination) physical, electrical, chemical, electromagnetic or biological. This interaction produces forces, electrical currents or chemical compounds which reveal information about the object.

Nanostructure 12 and supporting element 18 in combination can essentially be considered as a transducer for interacting with nanoscale environment 14. Conventional probe microscopy techniques are enabled and improved by the use of device 10, according to a preferred embodiment of the present invention.

Examples of conventional systems of this type include scanning tunneling microscopes, atomic force microscopes, scanning force microscopes, magnetic force microscopes and magnetic resonance force microscopes.

Device 10 is fundamentally different from conventional probe microscopy tips in its shape and its mechanical, electronic, chemical and/or electromagnetic properties. This difference permits new modes of operation of many probe microscopes, and new forms of probe microscopy. Device 10 is capable of imaging, at nanoscale resolution or greater, surfaces and other substrates including individual atoms or molecules such as biomolecules. Device 10 can replace relevant parts (e.g., tips) of any of the above systems.

In a preferred embodiment, supporting element 18 and/or nanostructure 12 may be pre-coated with a layer of conductive material in order to produce a good electrical contact therebetween.

Device 10 is particularly useful when used in tapping mode atomic force microscopy. In this mode, a change in amplitude of an oscillating cantilever driven near its resonant frequency is monitored as nanostructure 12 taps the surface of nanoscale environment 14. The sharp frequency response of high-quality cantilevers makes this technique exquisitely sensitive. Nanostructure 14 has the advantage that it is both stiff below a certain threshold force, but is compliant above that threshold force. More specifically, below the Euler buckling force, there is no bending of nanostructure 12. The Euler buckling force of nanostructure 12 is preferably in the one nano-Newton range. Once the Euler bucking force is exceeded, nanostructure 12 bends easily through large amplitudes with little additional force. In addition, nanostructure 12 is extremely gentle when laterally touching an object.

The result is that gentle, reliable atomic force microscopy imaging may be accomplished in the tapping mode with even extremely stiff, high-resonant frequency cantilevers. In contrast to the hard silicon pyramidal tip of existing systems, which can easily generate impact forces being larger than 100 nano-Newtons per tap, and therefore may substantially modify the geometry of soft samples such as large bio-molecules, nanostructure 12 serves as a compliant probe which moderates the impact of each tap on the surface.

An additional advantage of device 10 is its capability to explore regions of nanoscale environment 14 previously inaccessible to high resolution scanning probes. In this embodiment, nanostructure 12 is preferably of tubular shape so as to allow nanostructure 12 to penetrate into deep trenches of environment 14. Due to the above mention special mechanical characteristics of nanostructure 12 scanning force microscopy imaging of tortuous structures can be achieved without damaging nanostructure 12 or the imaged object.

Device 10 of the present invention can also be utilized to retrieve other types of information from nanoscale environment 14, such as, but not limited to, information typically obtained via conventional friction force microscopy. Friction force microscopy measures the atomic scale friction of a surface by observing the transverse deflection of a cantilever mounted probe tip. The compliance of nanostructure 12 above the Euler threshold as described above, provides for a totally new method of elastic force microscopy. By calibration of the Euler buckling force for nanostructure 12, and making appropriate atomic force microscopy measurements using nanostructure 12, one can obtain direct information about the elastic properties of the object being imaged.

Device 10 may also be used to perform nanoscale surface topography measurement. Motions of supporting element 18 can be calibrated by measurement of surfaces having known geometries (e.g., pyrolytic graphite with surface steps). Once properly calibrated, supporting element 18 and nanostructure 12 can provide precise measurement of the topography of surfaces and fabricated elements such as vias and trenches on integrated-circuit elements.

An additional use of device 10 is in mechanical resonance microscopy, which can be facilitated by mechanical resonances in nanostructure 12. These resonances may be utilized as a means of transduction of information about the object being sensed or modified. Such resonances, as will be known by one skilled in the art, can be sensed by optical, piezoelectric, magnetic and/or electronic means.

Nanostructure 12 can also act as a sensitive antenna for electromagnetic radiation. The response of nanostructure 12 to electromagnetic radiation may be recorded by detecting and measuring frequency currents passing therethrough as it and the object being sensed interact together in a nonlinear way with electromagnetic radiation of two or more frequencies. Via its interaction with electromagnetic fields of specified frequencies, nanostructure 12 may excite electronic, atomic, molecular or condensed-matter states in the object being examined, and the transduction of information about that object may occur by observation of the manifestations of these states.

Also of interest is the use of device 10 for probing biological systems. For example, device 10 can perform DNA sequencing by atomic force microscopy imaging of DNA molecules whereby nanostructure 12, due to its physical and chemical properties, permits the recognition of individual bases in the molecule.

In another biological application, device 10 can also be used for electrical or electrochemical studies of living cells. Knowledge of cell activity can be achieved, e.g., by measuring and recording electrical potential changes occurring within a cell. For example, device 10 of the present invention can accurately monitor specific cytoplasmic ions and cytosolic calcium concentrations with a spatial resolution far superior to those presently available. Living cells which can be studied using device 10 include, without limitations, nerve cell bodies and tissue culture cells such as smooth muscle, cardiac, and skeletal muscle cells.

Additionally, device 10 can be used, for example, to obtain and measure near field light from nanoscale environment 14. For the purpose of providing a self contained document a description of the near field phenomenon precedes the description of the presently preferred embodiment of the invention.

When light impinges on a boundary surface (such as the surface of nanoscale environment 14) having a varying refractive index at an angle which causes total reflection, the incident light is totally reflected on the boundary surface (reflection plane), in which case the light exudes to the opposite side of the reflection plane. This exuding light is called "near-field light." Other than the foregoing, the near-field light also includes light which exudes from a miniature aperture smaller than the wavelength of the light, through which the light is passed.

The near-field light can be utilized to analyze a surface state (shape, characteristics or the like) of a sample such as semiconductor materials, organic or inorganic materials, vital samples (cells) and the like. An ordinary optical microscope cannot measure a sample at a resolution higher than the wavelength of light due to diffraction of the light. This is called "diffraction limit of light." An analysis utilizing near-field light permits measurements at a resolution exceeding the diffraction limit of light.

According to a preferred embodiment of the present invention nanostructure 12 is adapted to collect near-field light of nanoscale environment 14. As the near-field light incidents on nanostructure 12, electronic excitation are induced therein. These electronic excitations cause a current to flow through nanostructure 12, toward detection system 16 which detects, records and/or analyzes the current.

It is appreciated that the above embodiments merely exemplify the potential use of device 10 for obtaining vital information from a nanoscale environment, previously unattained by conventional systems and apparati. The geometrical shape, nanometric size and physical properties of nanostructure 12 may also be used also for performing tasks, other than, obtaining information.

Nanostructure generated in accordance with the teachings of the present invention can also be utilized as part of a field emitting device.

Hence, according to another aspect of the present invention, there is provided a field emitter device, which is referred to herein as device 20.

Figure 2A:
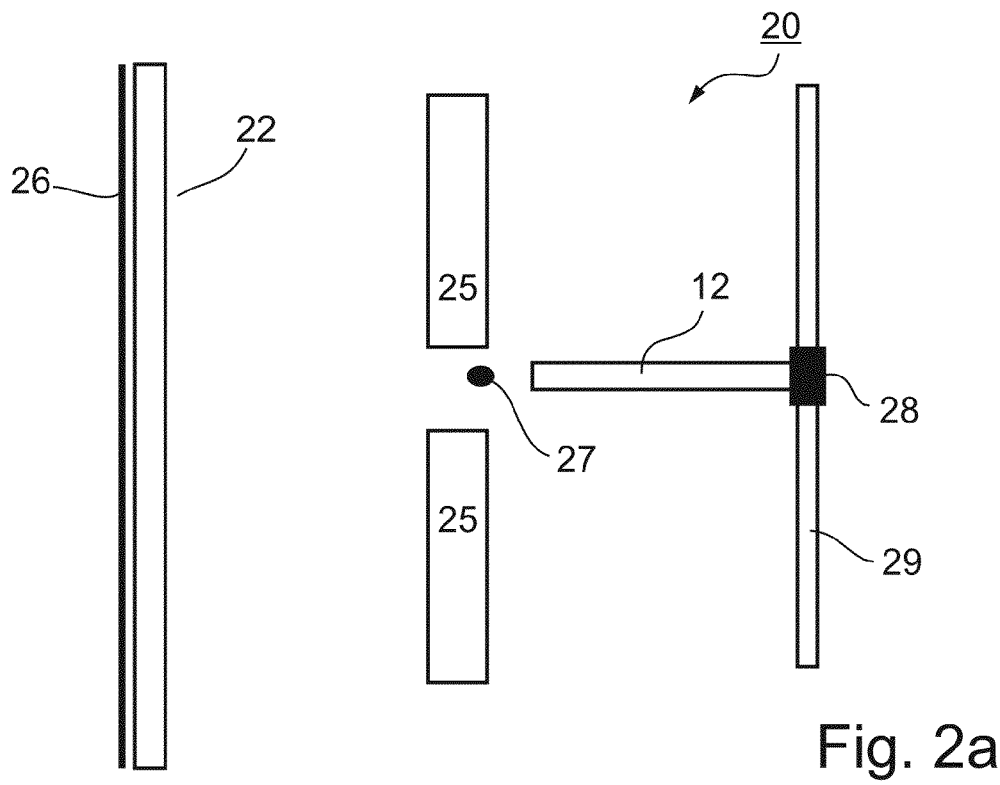

Reference is now made to FIG. 2a, which is a schematic illustration of a cross sectional view of device 20, according to a preferred embodiment of the present invention. Device 20 preferably comprises an electrode 22 and a nanostructure 12. Electrode 22 and nanostructure 12 are designed and constructed such that when an electrical field is formed therebetween, electrons 27 are extracted from nanostructure 12 by tunneling through the surface potential barrier. Once emitted from nanostructure 12, electrons 27 can be accelerated, redirected and focused so as to energetically excite atoms of a specific material, as further detailed hereinunder.

Figure 2B:
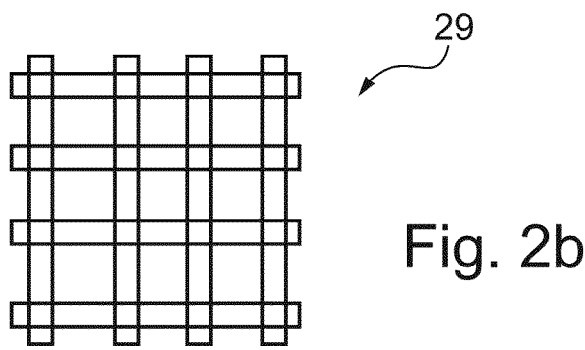

Device 20 may be integrated in many apparati, such as, but not limited to, a field emitter display. In this embodiment, a plurality of nanostructures may be positioned in cross points 28 of a matrix 29 of electrodes. Matrix 29, better illustrated in FIG. 2b, is formed of a plurality of row and column electrodes. Thus, each cross point 28 can be addressed by signaling the respective row and column electrodes. Upon a suitable signal, addressed to a specific cross point, the respective bundle of nanostructures 12 emits electrons, in accordance with the above principle.

Device 20 (or the apparatus in which device 20 is employed) may further comprise a substrate 26 having a fluorescent powder coating, capable of emitting light upon activation by the electrons. The fluorescent powder coating may be either monochromatic or multichromatic. Multichromatic fluorescent powder may be, for example, such that is capable of emitting red, green and blue light, so that the combination of these colors provides the viewer with a color image. Device 20 may further comprise a focusing element 25 for ensuring that electrons 27 strike electrode 22 at a predetermined location.

A special use of field emitter device, such as device 20, is in the area of electron beam lithography, in particular when it is desired to achieve a precise critical dimension of order of a few tens of nanometers. The present invention successfully provides an apparatus for electron emission lithography apparatus, generally referred to herein as apparatus 30. As further detailed hereinbelow, apparatus 30 is capable of transferring a pattern of a mask in a nanoscale resolution.

Figure 3:
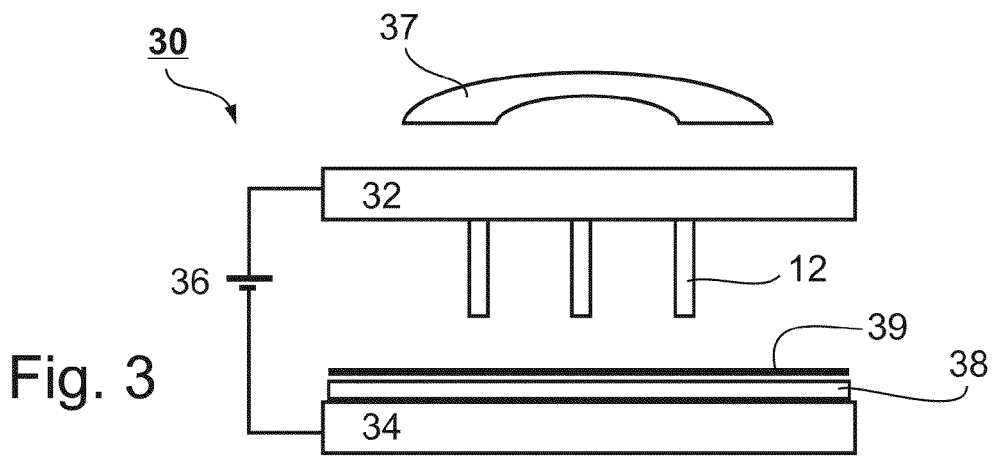

Reference is now made to FIG. 3, which is a schematic illustration of apparatus 30. Apparatus 30 comprises an electron emission source 32 and an electrically conducting mounting device 34. According to a preferred embodiment of the present invention, sources 32 includes one or more nanostructures 12, which, as stated, is composed of a plurality of peptides. Source 32 and mounting device 34 are kept at a potential difference, e.g., via a voltage source 36. The potential difference is selected such that electrons are emitted from source 32 (similarly to device 20).

A sample 38, on which an e-beam resist 39 to be patterned is formed, is disposed on mounting device 34, in a predetermined distance apart from a source 32. The electrons emitted from nanostructure 12 perform a lithography process on a sample 38 mounted thereon. Subsequently, if a developing process is performed, portions of resist 39 which were exposed to the emitted electrons remain when the resist 39 is negative, while portions of resist 39 not exposed to an electron beam remain when resist 39 is positive.

Source 32 and mounting device 34 are preferably positioned in a magnetic field generated by a magnetic field generator 37. Magnetic field generator 37 is designed to precisely control a magnetic field according to the distance between nanostructures 12 and resist 39, so that the electrons emitted from nanostructure 12 reach the desired positions on resist 39. Being charged particles moving in a magnetic field, the electrons are subjected to a magnetic force, perpendicular to their direction of motion (and to the direction of the magnetic field vector). Thus, a track of the movement of the electrons is controlled by magnetic field generator 37, which redirect the electron to the desirable position.

Consequently, the shape of nanostructures 12 can be projected upon sample 38, to thereby perform a lithographic process thereon. As described above, according to the present invention, since nanostructures 12 are used as electron emission sources, a lithography process can be performed with a precise critical dimension. In addition, since electrons emitted from nanostructures 12 carbon depreciate portions of resist 39 corresponding to nanostructure 12, a deviation between the center of a substrate and the edge thereof are substantially prevented.

An additional use of nanostructure 12 is in the field of information storage and retrieving.

Reference is now made to FIGS. 4a-b, which are schematic illustration of a memory cell, generally referred to herein as cell 40. In its simplest configuration, cell 40 comprises an electrode 42 and a nanostructure 12. Nanostructure 12 preferably capable of assuming one of at least two states. For example, as already described hereinabove, nanostructure 12 has the capability to deflect when the Euler buckling force is exceeded, thus, a first state of nanostructure 12 can be a non-deflected state (when an external force applied on nanostructure is below Euler buckling force) and a second state of nanostructure 12 can be a deflected state (when the external force is above or equals the Euler buckling force).

Nanostructure 12 is preferably be suspended by one or more supports 44 over electrode 42. Nanostructure 12 may be held in position on support(s) 44 in more than one way. For example, nanostructure 12 is held in position on support(s) 44 by or any other means, such as, but not limited to, by anchoring nanostructure 12 to support(s) 44. The holding of nanostructure 12 in its place on support(s) 44 can also be facilitated by chemical interactions between nanostructure 12 and support(s) 44, including, without limitation, covalent bonding.

Electrode 42, nanostructure 12 and the distance therebetween are preferably selected such that electrical current flows through electrode 42 and/or nanostructure 12, generates an electric force on nanostructure 12 which is larger than the Euler buckling force. Thus, temporarily electric current(s) transform nanostructure 12 from the first state (FIG. 4a) to the second state (FIG. 4b).

A plurality of cells like cell 40 can be incorporated to provide an electromechanical memory array. Each cell in the array can be in either a first state or a second state thus can store a binary information of a first type of datum (say, "0") and a second type of datum (say, "1"). As the size of nanostructure 12 is in the nanometric scale, many such cells can be integrated in a single array so that the information storage capacity of the entire array is substantially larger, or at least equivalent to modern memory devices. Each cell may be read or written by applying currents and or voltages to electrode 42 or nanostructure 12.

More specifically, when nanostructure 12 is in a non-deflected state (FIG. 4a), cell 40 is characterized by an open circuit, which may be sensed as such on either nanostructure 12 or trace electrode 42 when so addressed. When nanostructure 12 is in a deflected state (FIG. 4b), cell 40 is characterized by a rectified junction (e.g., Schottky or PN), which may be sensed as such on either nanostructure 12 or trace electrode 42 when so addressed.

As will be appreciated by one ordinarily skilled in the art, cell 40 (and therefore an integrated array of a plurality of such cells) is characterized by a high ratio of resistance between "0" and "1" states. Switching between these states is accomplished by the application of specific voltages across nanostructure 12 or electrode 42. For example, "readout current" can be applied so that the voltage across a respective junction is determined with a "sense amplifier." It will be appreciated that such reads are non-destructive. More specifically, unlike DRAM systems, where write-back operations are required after each read, cell 40 retains its state even once read is performed.

According to another aspect of the present invention, there is provided an electronic device, for switching, inverting or amplifying, generally referred to as device 50.

Reference is now made to FIG. 5a, which is a schematic illustration of device 50. Device 50 comprises a source electrode 52, a drain electrode 54, a gate electrode 56 and a channel 58. One or both of gate electrode 56 and channel 58 may comprise a nanostructure (e.g., nanostructure 12) which is composed of a plurality of peptides, as further detailed hereinabove. For example, in one embodiment channel 58 is a nanostructure and gate electrode 56 is preferably layer of $SiO_2$ in a silicon wafer.

In its simplest principle, device 50 operates as a transistor. Channel 58 has semiconducting properties (either n-type or p-type semiconducting properties) such that the density of charge carriers can be varied. A voltage 57 is applied to channel 58 through gate electrode 56, which is preferably separated from channel 58 by an insulating layer 59. When the voltage of gate electrode 56 is zero, channel 58 does not contain any free charge carriers and is essentially an insulator. As voltage 57 is increased, the electric field caused thereby attracts electrons (or more generally, charge carriers) from source electrode 52 and drain electrode 54, so that channel 58 becomes conducting.

Thus, device 50 serves as an amplifier or a switching device where, voltage 57 of gate electrode 56 controls the current flowing from source electrode 52 and drain electrode 54, when a bias voltage 53 is applied therebetween.

Two devices like devices 50 may be combined so as to construct an inverter. Referring to FIG. 5*b*, in this embodiment, a first such device (designated 50*a*) may include a channel having an n-type semiconducting properties and a second such device (designated 50*b*) may include a channel having an p-type semiconducting properties. Devices 50*a* and 50*b* are preferably connected such that when bias voltage 53 is applied between the source of device 50*a* and the drain of device 50*b*, the combined device serves as an inverter between input signal 51 and output signal 55.

Following are several aspects of the present invention in which nanostructure 12 is primarily exploited for performing mechanical tasks.

According to an additional aspect of the present invention, there is provided a mechanical transmission device, generally referred to herein as device 60.

Reference is now made to FIG. 6, which is a schematic illustration of device 60, according to a preferred embodiment of the present invention. Device 60 comprises a first nanostructure 12 and a second nanostructure 62, which, as stated are composed of a plurality of peptides. First 12 and second 62 nanostructures are operatively associated thereamongst such that a motion of first nanostructure 12 generates a motion of second nanostructure 62. Both first 12 and second 62 can have any shape suitable for transmitting motion, such as, but not limited to, a tubular, spherical or planar shape. To facilitate the operative association, one or more molecules 64 (e.g., antibodies, ligands, DNA, RNA, or carbohydrates) can be attached to the external surface of first 12 and/or second 62 nanostructures.

Hence, device 60 can operate as a nanomachine which could self-repair or adapt to the environment. Preferably, first 12 and/or second 62 nanostructures include oppositely charged atoms on their antipodes, so that an electric field can generate a circular motion. Being of a nanometric size, an extremely small magnitude of electric field is sufficient for rotating the nanostructures, in an extremely large angular velocity, typically in the Giga-Hertz range.

Another mechanical application in which nanostructure 12 can be used is illustrated in FIG. 16. In this aspect of the present invention nanostructure 12 is exploited for the purpose of manipulating nanoscale objects. A potential application of the present aspect of the invention is in the area of assembling nanoelectronic circuit (see, e.g., cell 40 or device 50 hereinabove) when nanoscale objects are to be precisely located in a predetermined location.

FIG. 16 illustrates a nanoscale mechanical device 70, which comprises at least one nanostructure 12 designed and configured for grabbing and/or manipulating a nanoscale object 74. Such operation may be achieved, for example, using two nanostructures 12, preferably tubular nanostructures, mounted on a mounting device 72, whereby nanostructures 12 perform a constrained motion to grab object 74.

Mounting device 72 can be, for example, a tip end of an atomic force microscopy cantilever, so that one or both of nanostructures 12 can also be utilized as an atomic force microscopy probe. In use, nanostructures 12 first scan (e.g., as an atomic force microscopy probe) the region where object 74 is expected, thus confirming the position and shape thereof. This scan me be performed in any method known in the art, such as, but not limited to, using a three-dimensional driving mechanism 78.

The motion of nanostructure 12 may be controlled, for example, by a voltage source 76 which generates an electrostatic force between nanostructures 12. Thus, by activating voltage source 76 nanostructures 12 can close or open on object 74.

Once nanostructure 12 grip object 74, which, as stated, has been marked by the atomic force microscopy procedure, mounting device 72 can be moved by three-dimensional driving mechanism 78, to a desired location. Subsequently nanostructures 12 are further opened, thus releasing object 74 in its appropriate location. In cases where object 74 fails to separate from nanostructures 12, e.g., due to Van der Waals forces between object 74 and nanostructures 12, a further voltage can be applied between nanostructures 12 and the desired location, so that object 74 is released by an electrostatic attractive force.

As stated, the nanostructure of the present invention can also be used for reinforcing other materials, such as, but not limited to, polymers. Thus, according to yet an additional aspect of the present invention there is provided composition, in which a polymer is combined with the nanostructure of the present invention. Preferably, the nanostructure is chemically bonded to or integrated within the polymer chains via one or more chemical bond types.

Several attachment configurations can be utilized in order to reinforce polymer chains.

For example, the nanostructure can be linked to one or more chain-terminating group of the polymer chain or to residues of internal polymer groups. The polymer component of the composition of the present invention preferably comprises polymers, including copolymers, which are capable of chemically bonding with the peptides of the nanostructure, or those polymers that can be prepared from one or more monomer precursors capable of bonding with the peptides of the nanostructure either prior to or during polymerization. Representative examples of polymers which may be used include without limitation polyethylene glycol (PEG), polysaccharides, DNA, RNA, poly amino-acids, peptide nucleic acid (PNA).

The composition described above, can be used for manufacturing many forms of articles, such as filaments, carpets, ropes and the like.

A fiber can be formed from the polymer-nanostructure composition by cutting the composition into chips and drying. These chips can then be heated under pressure to bond the chips into a plug. This plug can then be heated to a molten state, passed through a mesh screen, and forced through an extrusion orifice. The filament formed by the molten composite material can then be pulled away from the orifice and wound onto a bobbin. Such fibers can be incorporated into bulked continuous filament, and made into carpets, ropes and the like.

Alternatively, the composition describe above can be used as an injection moldable resin for engineering polymers for use in many applications, such as, but not limited to, filters, solenoids and the like.

The nanostructure of the present invention can also be dispersed throughout a matrix material to thereby form a free-form structure. Constructing and arranging composite nodal elements to define a structure circumvents the common practice in the industry of post-fabrication processing operations. Initially, a structure is often fabricated in a mold or by machining and then subjected to post-fabrication processing operations. Post-fabrication processing operations refer to added steps required beyond initial fabrication so that the structure exhibits desired dimensions and tolerance. Typically, post-processing operations include for example, among others, machining, cleaning, polishing, grinding, deburring and hole drilling so as to achieve desired dimensions and tolerance of a fabricated structure.

Following is a description of an additional embodiment of the present invention in which the nanostructures are used for the purpose of delivering energy from one location to the other.

In many industries, there is a great need for more efficient heat transfer fluids. Heat transfer fluids used in today's conventional thermal systems have inherently poor heat transfer properties. Often, millimeter- or micrometer-sized particles are suspended in heat transfer fluids so as to increase the capability of the fluid to deliver heat. The ratio of surface area to volume of the nanostructure of the present invention is about three orders of magnitudes larger than that of micrometer-sized particles. Since heat transfer occurs on the surface of a fluid, this feature of the present invention can be used for significantly enhancing heat conduction properties of cooling fluids.

Thus, according to a further aspect of the present invention there is provided, a nanofluid, comprising the nanostructures of the present invention suspended in a fluid. The nanofluid of the present invention is characterized extreme stability and ultra-high thermal conductivity.

The present invention successfully provides a heat transfer device 80 which exploits the above mentioned thermal properties of the nanofluid.

Reference is now made to FIG. 8, which is a schematic illustration of device 80. Device 80 comprises a nanofluid 82 and a channel 84 for holding nanofluid 82. As stated, nanofluid 82 comprises nanostructures 12 suspended in a fluid 86, where at least a portion of nanostructures 12 is composed of a plurality of peptides, as further detailed hereinabove and in accordance with the present invention. Channel 84 is preferably constructed such that heat is transferred by nanofluid 82, and, in particular, by nanostructure 12, from a first end 87 to a second end 88 of channel 84.

Channel 84 is preferably in a micrometer size (i.e., a microchannel) or a nanometer size (i.e., a nanochannel), both are known in the art. In the embodiment in which channel 84 is a nanochannel, the diameter thereof is larger than the diameter of the largest nanostructure, so as to allow nanofluid 82 to flow freely through channel 84.

Device 80 may further comprise a locomotion system 89 for generating locomotion of nanofluid 82 within channel 84. System 89 may operate in any way known in the art for generating locomotion of nanofluid 82. For example, in one embodiment, the locomotion of nanofluid 82 can be achieved by an under-pressure formed in channel 84, in which case system 89 generates under-pressure. In another embodiment, fluid locomotion can be achieved by dielectrophoretic forces applied thereon, in which case system 89 can be realized, for example, as a mechanism for generating a non-uniform electric field.

Following is a description of additional embodiments of the present invention in which the nanostructures described hereinabove are coated by a conducting shell to form the nanoshell further detailed hereinabove.

Hence, according to yet another aspect of the present invention there is provided a composition for modulated delivery of a chemical to a predetermined location. The composition comprises a plurality of nanoshells, each nanoshell having a nanostructure core and a conductive shell which is capable of converting incident radiation into heat energy. The nanostructure core is composed of a plurality of peptides, as further detailed hereinabove. The composition further comprises a medium having the chemical and a thermally responsive material (e.g., a thermally responsive hydrogels) in thermal contact with the nanoshells.

Composites of thermally responsive hydrogels are known in the art. For example, copolymers of N-isopropylacrylamide (NIPAAm) and acrylamide (AAm) exhibit a lower critical solution temperature (LCST) that is slightly above body temperature. When the temperature of the copolymer exceeds the LCST, the hydrogel collapses, causing a rapid release or burst of any soluble material held within the hydrogel matrix.

The nanoshells serve as heat transfer agents within the polymer matrix. Each of the nanoshells may also include a targeting component, such as an affinity component having an affinity to the cells in the location of interest. Being of nanometric diameter, the nanoshells have well defined wavelength absorbance maxima across the visible and infrared range of the electromagnetic spectrum. Preferably, the conductive shell of the nanoshells is made of gold. A gold shell can be fabricated, for example, by seeding the amine groups OF the nanostructure core with colloidal gold; additional colloidal gold is added via chemical reduction in solution, to form the gold shell layer.

The wavelength of maximum optical absorption of each nanoshell is determined by the ratio of the core radius to the shell thickness. Each of these variables (core radius and shell thickness) can be independently controlled during fabrication of the nanoshells. Varying the shell thickness, core diameter, and the total diameter of the nanoshell, allows the optical properties of the nanoshells to be tuned over the visible and near-infrared spectrum.

In order to convert light energy into heat, administered nanoshells are exposed to light at an appropriate wavelength (e.g., 800-1200 nm) which is transmitted through tissue. The generated heat causes collapse of the hydrogel in the vicinity of the nanoshell causes significantly enhanced release of chemicals and proteins of varying molecular weight from the new composite hydrogels.

Since it is capable of converting light energy into heat, the nanoshell of the present invention can be used to induce localized hyperthermia in a cell or tissue of an individual and thus can be utilized as therapeutic agent in treatment of various diseases such as hyperproliferative diseases, as detailed hereinbelow.

For example, an individual having cancer can be administered with a therapeutic effective amount of the nanoshells of the present invention using a suitable administration route and thereafter exposed to electromagnetic radiation in the resonance frequency of the nanoshells, e.g., using a continues wave or pulse laser device, for a time period of, say, about 5-30 minutes to thereby convert the electromagnetic radiation into heat energy. The generated heat may is preferably sufficient to perform therapeutic treatment, e.g., to kill the cells, if so desired.

Preferably, the electromagnetic radiation is in the near infrared range. Such radiation is advantageous for its ability to penetrate tissue. Other types of radiation can also be used, depending on the selection of the conductive shells and the targeted cells. Examples include x-rays, magnetic fields, electric fields and ultrasound.

As stated, the method may be used for destroying living cells. In this embodiment, each of the nanoshells may include an affinity component having affinity to the living cells to be destroyed. Thus, the present invention can be used to treat many types of cancers, such as, but not limited to, vaginal cancer, vulvar cancer, cervical cancer, endometrial cancer, ovarian cancer, rectal cancer, salivary gland cancer, laryngeal cancer, nasopharyngeal cancer, many lung metastases and acute or chronic leukemia (e.g., lymphocytic, Myeloid, hairy cell).

According to a preferred embodiment of the present invention, the affinity component of the nanoparticles includes a moiety which may be, for example an antibody, an antigen, a ligand or a substrate.

The following lists primary antibodies known to specifically bind their associated cytological markers and which are presently employed as affinity components in immunohistochemical stains used for research and, in limited cases, for diagnosis and therapy of various diseases. Anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oncoprotein (p21) antibody, anti-Lewis X (also called CD15) antibody, anti-Ki-67 antibody (cellular proliferation), anti-PCNA (multiple cancers) antibody, anti-CD3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblasic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salvary, glial cells), anti-tau antigen antibody (Alzheimer's disease), anti-fibrin antibody (epithelial cells), anti-keratins antibody, and anti-Tn-antigen antibody (colon carcinoma, adenocarcinomas, and pancreatic cancer).

Other applications of the nanostructures of the present invention include use thereof in biomedical sciences and in biotechnology such as their use as vehicles for enzyme encapsulation [Chang (2001) Mol. Biotechnol. 17:249-260], DNA transfection [Kneuer (2000) Bioconj. Chem. 11:926-932; Rader (1997) Science 810-814; Koltover (1998) Science 281: 78-81], scaffolds for tissue building, biosensors [Cao (2002) Science 297:1536-1540; Demers (2002) Science 296:1836-1838; Park (2002) Science 295:1503-1506] and drug delivery [Ulrich (1999) Chem. Rev. 99:3181-3198; Lee (2002) Biomacromolecules 3:1115-1119; Murthy (2002) J. Am. Chem. Soc. 124:12398-12399]. For example, drugs can be incorporated onto the biodegradable nanospheres of the present invention, to thereby allow for timed release of the drug as the nanosphere degrades. The conditions which allow degradation can be adjusted by varying the chemical bonding within the nanostructure. For example, when acid-labile bonds are used, the nanostructures of the present invention will degrade in an acidic environment such as would exist in a site of inflammation or in tumor cells. Alternatively, the nanostructures of the present invention can be coated with viral peptide sequences which promote membrane-permeation. Finally, surface functionalized nanostructures of the present invention can also be used to deliver genetic material into living cells (i.e., transfection).

In any of the above embodiments, the nanostructures can be coated by any suitable material, e.g., a conductive material (as in the case of the nanoshells), a semiconductive material or a dielectric material, and can be bounded to other molecules to achieve desired electrical, mechanical, chemical or biological properties. For example, the nanostructures of the present invention can be coated by silver, gold and other conductive materials.

It is expected that during the life of this patent many relevant structures of nanometric size will be developed and the scope of the term nanostructure is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Nanotubes Self-Assembly of Alzheimer's β-Amyloid Core Recognition Element

Materials and Experimental Procedures
Material—
Peptides (NH$_2$-Phe-Phe-COOH, SEQ ID NO: 1) were purchased from Bachem (Budendorf, Switzerland). Freshly prepared stock solution was prepared by dissolving lyophilized form of the peptide in 1,1,1,3,3,3,-Hexafluoro-2-propanol at a concentration of 100 mg/ml. To avoid any pre-aggregation, fresh stock solution were prepared for each experiment.
Transmission Electron Microscopy (TEM)—
Peptide stock solution was diluted to a final concentration of 2 mg/ml in double distilled water, then a 10 μl aliquot of the peptide suspension was placed on a 200 mesh copper grid, covered with carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.
Scanning Electron Microscopy (SEM)—
Peptide stock solution was diluted to a final concentration of 0.5 mg/ml in double distilled water. Thereafter a 30 μl aliquot was allowed to dry on microscope glass cover slips. The sample was than coated with gold. Scanning electron microscopy images were made in JSM JEOL 6300 SEM operating at 20 kV.
Congo Red Staining and Birefringence—
Peptide stock solutions were diluted to a final concentration of 0.25 mg/ml in double distilled water. Thereafter a 10 μl aliquot was allowed to dry on glass microscope slide. Staining was effected by adding a solution of 80% ethanol saturated with Congo red and NaCl. Birefringence was determined with a SZX-12 Stereoscope (Olympus, Hamburg, Germany), equipped with a polarizing stage.
Dynamic Light Scattering—
Freshly prepared peptide stock solution at a concentration of 10 mg/ml were diluted in double distilled water to a final concentration range of 0.01 to 0.5 mg/ml. Experiments were conducted with protein solutions DynaPro MS-800 instrument (Protein Solutions, Lakewood, N.J.). Autocorrelation data was fitted using dynamics V6 software to derive hydrodynamic diameters.
Fourier Transform Infrared Spectroscopy—
Infrared spectra were recorded using Nicolet Nexus 470 FT-IR spectrometer with DTGS detector. Sample of aged peptide solution, taken from electron microscopy experiment was vacuum dried on CaF$_2$ plate to form a thin film. Peptide deposits were resuspended in double distilled water and dried. The suspension procedure was repeated twice to ensure maximal hydrogen to deuterium exchange. Measurements were effected using a 4 cm$^{-1}$ resolution and 2000 scan averaging. The transmittance minimum values were determined by OMNIC analysis software (Nicolet).
Results
Very concentrated peptide solution (i.e., 100 mg/ml) were prepared by dissolving the lyophilized peptide in 1,1,1,3,3,3 hexafluoro-2-propanol. While the peptide appeared to be highly soluble in the organic solvent, a rapid assembly into ordered semi-crystalline structures was visually observed within seconds after dilution into the aqueous solution at a final mM concentration range. Assembly into supramolecular structures was determined within minutes at the μM range, using dynamic light scattering analysis (data not shown).
Transmission Electron microscopy indicated that the peptides form well-ordered, thin (i.e., 50-60 nm in diameter) and elongated (i.e., several micron long) assemblies (FIG. 9a). The formed structures were ordered but clearly different from typical amyloid fibrils, as they formed stiff tubules which lacked a typical branching and curving. Interestingly, these assemblies resembled the previously reported tubules formed by hepta-octopeptides [Vauthey (2002) Proc. Natl. Acad. Sci. USA 99:5355].
SEM electron microscopy was effected to study the tubular structures formed by the diphenylalanine peptides. As shown in FIG. 9b, SEM analysis indicated a typical nanotubular structures similar to those previously reported [Vauthey (2002) Proc. Natl. Acad. Sci. USA 99:5355].
To elucidate the molecular configuration of the assembled structures, fourier-transformed infrared spectroscopy was effected. As shown in FIG. 9c, the spectral analysis of the assemblies indicated a sharp 1630 cm$^{-1}$ pick at the amide I region. This pick was consistent with a β-sheet-like conformation of the single amide bond, as was suggested for peptide nanotubes built from larger building blocks [Ghadiri (1993) Nature 366:324; Vauthey (2002) Supra] and for amyloid fibrils [Reches (2002) J Biol Chem 277(38):35475-80].

Congo red staining of the supramolecular structures formed by the dipeptides of the present invention showed a green-gold birefringence typical of amyloid structures (FIG. 9d).

Altogether, these results show that a small recognition motif of the β-amyloid polypeptide contains all molecular information required to mediate self-assembly into regular structures. Noteworthy is the fact that the tubular structures were observed with SEM in the absence of coating, suggesting that such structures can be used to as conductive tubes.

The persistence length of the nanotubes appeared to be at the order of micrometers as evident by the microscopic observation. It is worth noting, that the formation of the tubular structures was very efficient. Most assemblies, as observed by TEM analysis had tubular structures and almost no amorphous aggregates were detected (<1%). This is in mark difference to other peptide assemblies (such as amyloid fibrils) in which a mixture of ordered and aggregated structures maybe observed. High resolution TEM (HR-TEM; FIG. 10b) provided further indication of the regular structures of the tube walls. The formed structures were highly ordered and appeared to be rather stiff, but without the usual branching and curving typical of amyloid fibrils. On the other hand, the assemblies showed some morphological similarity in terms of size and tubular structures to the recently observed peptide nanotubes that are formed by a much longer surfactant-like hepta- to octapeptides [Vauthey (2002) Supra]. These structures are different from the first reported peptide nanotubes that were formed by cyclic polypeptides made of alternating D- and L-amino acids [Hartgerink (1996) J. Am. Chem. Soc. 118:43].

Scanning electron microscopy (SEM) was used to further study the tubular structures (FIGS. 11a-b). The nanotubes were applied on a glass cover slip coated with gold and imaged by SEM. The low magnification micrographs of areas filled with individual nanotubes (FIG. 11a), substantiated that the tubes were relatively homogenous and evidently individual entities with a persistence length in the order of micrometer. FIG. 11c shows the statistical distribution of the diameters of the nanotubes. In this context, it is worth noting that the crystal structure of the diphenylalanine peptide, as formed by evaporation of aqueous solution at 80° C., showed a crystal packing of aligned and elongated long hollows [Gorbitz (2001) Chemistry 38:6791]. These structures were also referred to as peptide nanotubes. However, it is very clear from the present structural analysis, that the crystal packing of the peptide represents a completely different molecular arrangement as compared to the self-assembled individual tubular structures. Higher magnification SEM analysis also indicated a typical nanotubular structures that resembled, to some extent, a class of peptide nanotubes that were recently reported [Vauthey (2002) supra], albeit apparently stiffer and discrete (FIG. 11b).

For other applications, such as the assembly of nanotube based biosensors or hollow tubing of nanofluidic circuits, enzymatically stable nanotubes are desired. To assemble such stable tubes, proteolytically stable building blocks based on the D-amino-acids analogue of the peptide, NH2-D-Phe-D-Phe-COOH (SEQ ID NO: 8) were used. This peptide formed nanotubes with the same structural features as the corresponding L-amino-acids peptide (FIG. 12a). Remarkably, following one hour of incubation of the peptide with 0.02 mg/ml of Proteinase K, no tubular structures were observed by electron microscopy examination, as compared to hundreds of tubular structures observed prior to proteolysis. In a mark difference, no significant variation could be observed before and after the incubation of the D-Phe-D-Phe peptide with the enzyme.

In light of the formation of nanotubes by such short dipeptide, the ability of other aromatic dipeptides (e.g., Phe-Trp, Trp-Tyr, Trp-Phe, and Trp-Trp) was tested under similar conditions. As shown in FIG. 12b and FIGS. 13a-c, nanoscale tubular structures were also observed upon assembly of the Phe-Trp peptide (FIG. 12b). However, a significant amount of amorphous aggregates were also observed. This is in mark difference to the Phe-Phe peptide in which practically only tubular structures were observed.

A mechanical model for the formation of the peptide nanotubes described above is provided in FIG. 14. Briefly, a stacking interaction between aromatic moieties of the peptides is suggested to provide energetic contribution as well as order and directionality for the initial interaction. The spectroscopic evidence of β-sheet conformation of the single amide bond is reflected by an extension of the amino acids to the opposite sides and the formation of an extended pleated sheet that is stabilized by hydrogen bonds and aromatic stacking interactions. The formation of the tubular structures may occur by a closure of the extended sheet as previously suggested [Reches and Gazit (2004) Nano letters 4: 581-585].

Example 2

Formation of Fullerene-Like Closed-Cage Structures by Self-Assembly of Aromatic Dipeptides Materials and Experimental Procedures
Materials—
The diphenylalanine and diphenylglycine peptides were purchase from Bachem (Bubendorf, Switzerland, SEQ ID NOs: 1 and 6, respectively). The CFF peptide was purchase from SynPep (Dublin Calif., USA). Fresh stock solutions of the diphenylalanine and the diphenylglycine were prepared by dissolving lyophilized form of the peptides in 1,1,1,3,3,3-hexafluoro-2-propanol (HFP, Sigma) at a concentration of 100 mg/ml.

The CFF peptide was prepared by dissolving lyophilized form of the peptide in HFP and 25% dithiothreitol, 1 M in ddH2O to a final concentration of 25 mg\ml. To avoid any pre-aggregation, fresh stock solutions were prepared for each experiment. The peptides stock solutions were diluted into a final concentration of 2 mg/ml in double distilled water.

Chemical Modification of an Amine to a Thiol—
The diphenylalnine peptide was dissolved in HFP to a concentration of 100 mg/ml. This was followed by the addition of 2 μl of the solution to 8 μl of 100 mg/ml 2-iminothiolane (Sigma) dissolved in dimethylsulfoxide (DMSO) with 2% N,N-diisopropylethylamine (DIAE). Double distilled water was added to give a final peptide concentration of 2 mg/ml. Two control reactions were effected to exclude components of the reaction mixture in the assembly of the peptides; Essentially, in the first control experiment the reaction mixture was prepared without the addition of DIAE. In the second control experiment, the reaction mixture was prepared without the addition of DIAE and 2-iminothiolane.

Transmission Electron Microscopy—
Following 24 hours of incubation at room temperature, a 10 μl aliquot of the peptide solution was placed on 200 mesh copper grid. After 1 minute, 14 excess fluid was removed. In negative staining experiments, the grid was stained with 2% uranyl acetate in water and after two minutes excess fluid was removed from the grid. Samples from the chemical reaction that modifies amines to thiols were not negatively stained with uranyl acetate. Samples were viewed using a JEOL 1200EX electron microscope operating at 80 kV.

Atomic Force Microscopy—

AFM samples were prepared by drying the peptide solutions on TEM grids, without the staining procedure. Semi-contact mode imaging was performed on a P47 solver—NT-MDT (Moscow, Russia), by using OTESP integrated cantilever probes with resonance frequency 390 kHz.

High Resolution Scanning Electron Microscopy—

TEM grids that were used for AFM analysis were viewed using JSM-6700 Field Emission Scanning Electron Microscope equipped with cold filed emission gun operating at 1 kV.

Stability in Alkaline and Acidic Conditions—

In the case of stability to alkaline conditions, NaOH was added into the peptide nanosphere solution to a final concentration of 1 M NaOH. In the case of stability in acidic conditions, TFA was added to the nanostructure solution to a final concentration of 10% TFA. After 5 hours peptide solutions were placed on TEM grids and analyzed by TEM.

Results

In search for the simplest biomolecular self-assembled system, the most generic form of an aromatic dipeptide, the diphenylglycine was designed and synthesized (FIG. 15b). The diphenylglycine offers similar molecular properties as the diphenylalanine peptide albeit its molecular structure is more rigid with a lower degree of freedom due to the lack of rotational freedom around the additional C—C bond and the higher steric hindrance of the molecule.

Structural analysis using TEM (transmission electron microscopy) revealed that under the same conditions that peptide nanotubes were formed by the diphenylalanine, spherical nanometric structures self-assembled by the diphenylglycine peptide (FIGS. 15c-d). These nanometric particles existed as individual entities and had a uniform spherical appearance as seen by TEM visualization (FIG. 15d). The assembly of the spherical particles was very efficient and regular, as could be seen using low magnification TEM analysis (FIG. 15d). The efficiency and regularity were similar to those observed with the peptide nanotubes (see Example 1, above).

In order to further examine the three dimensional characteristics of the novel nanoparticles they were subjected to analysis by SEM (scanning electron microscopy). Cold field emission gun (CFEG) high-resolution scanning electron microscope (HRSEM) confirmed the three dimensional spherical shape and the regularity of the self assembled nanostructures (FIG. 16a).

In addition, AFM (atomic force microscopy) analysis was employed to get an independent indication about the topography of nanostructures. The AFM analysis clearly confirmed the three dimensional spherical configuration of the nanostructures (FIGS. 16b-c).

It will be appreciated that while AFM is a less suitable tool to determine the exact dimensions of the structures at the horizontal and vertical axis due to tip convolution, it is an excellent method to determine the height of nanostructures at the Z-range. Indeed, AFM analysis clearly indicated that the spheres are about 90 nm in height (FIG. 16b), which is consistent with both TEM and SEM analysis.

The stability of the newly discovered nanoparticles under extreme chemical conditions was addressed as well (FIGS. 17a-b). The nanospheres were found to be stable under acidic conditions following incubation for 5 hours at 10% TFA as they maintained their configuration and uniform structure (FIG. 17a). The stability of the nanospheres was also tested under alkaline conditions i.e., 1M NaOH for 5 hours (FIG. 17b). In the presence of NaOH, the nanosphere structure appeared to be more uniform while having a smaller diameter. This remarkable stability of the nanoparticles is very intriguing both from the scientific point of view as well as the technological one. The significant stability of the peptide nanostructures is rare but consistent with the structural stability of amyloid fibrils as was recently reported [Scheibel (2003) Proc. Natl. Acad. Sci. USA 100:4527].

These results are in accordance with the apparent role of peptide motifs in the molecular recognition and self-assembly of amyloid fibrils. Moreover, the unusual stability of the peptide nanostructures is extremely useful for their use as part of a combined (bio)organic and/or inorganic nanoscale fabrication process, including optic and electron-beam lithographic protocols. Although biologically based scaffolds offer many advantages to nanotechnology, their relative instability in general questions their ability to serve in robust and long-lasting nanodevices.

The newly described peptide nanostructures offer both molecular recognition and chemical flexibility of biological nano-objects, together with stability that is compatible with industrial procedures and the requirements for robust and stable devices.

In parallel experiments, the ability of the cysteinediphenylalanine tripeptide (CFF, SEQ ID NO: 7, FIG. 18a) to form peptide nanotubes was addressed. The rationale behind these studies was to introduce a thiol group into the nanotubes that would allow their covalent attachment to fabricated gold electrodes in nanodevices. However, as shown in FIGS. 18b-c, CFF peptide did not self-assemble into nanotubes but rather into nanospheres that were very similar to those formed by the diphenylglycine peptide.

To study whether the spherical structures that were formed by the CFF peptide were the result of the peptide length or rather the presence of the thiol group, an amine was chemically modified into a thiol in the context of the diphenylalanine peptide (FIG. 18d). For that purpose, 2-iminothiolane (Traut's reagent), which reacts with the single primary amine in the diphenylglycine and introduces a sulfhydryl group was used. The peptide was reacted with the reagent in organic solvent mixture that was then followed by dilution into an aqueous solution that allowed the self-assembly process. As shown in FIG. 18d, the addition of a thiol group to the diphenylalnine peptide transformed the geometry of the assembled structures from nanotubular into spherical ones. As a control, the same reaction mixture was used but without the addition of the N,Ndiisopropylethylamine base that is required for the reaction. Under these conditions only nanotubular structures were observed.

The study of inorganic nanotubes and fullerene-like structures, indicated that the formation of fullerenes is not unique to carbon and is attributed to a genuine property of two-dimensional (i.e., layered) compounds [Tenne (1992) Nature 360:444; Feldman (1995) Science 267:222; Chhowalla (2000) Nature 407:164; Tenne (2002) Chemistry 23:5293].

As mentioned hereinabove, it is highly likely that the novel type of peptide nanotubes is being formed by a closure of a two dimensional layer. The results described herein provide further experimental support to this notion. It appears that the energetic contribution provided by the disulphide bridge formation may allow closure of the two-dimensional layer into more closely packed spherical structures. Taken together, the results clearly suggest that aromatic peptide assemblies represent a novel class of nanostructures that are mechanistically closely-related to aromatic carbon nanotubes and fullerenes and to their related inorganic nanotubes and fullerene-like structures. Applications, methodologies, and theories that were applied to the study of carbon and inorganic nanostructures should be of great importance for future exploration and utilization of the peptide nanostructures. These properties of the peptide nanostructures, taken together with their biological compatibility and remarkable thermal and chemical stability, may provide very important tools for future nanotechnology applications.

Example 3

Formation of Tubular Nanostructures by Self-Assembly of Polyphenylalanine Peptide The ability of polyphenylalanine peptides of 50-136 amino acids to self assemble into discrete nanotubes was examined.

Materials and Experimental Procedures

Materials—

The Polyphenylalanine peptide was purchase from Sigma-Aldrich. Fresh stock solution was prepared by dissolving lyophilized form of the peptide in dichloroacetic acid at a concentration of 5 mg/ml and was incubated for an hour in a water bath pre heated to 85° C. To avoid any pre-aggregation, fresh stock solutions were prepared for each experiment. The peptide stock solution was diluted into double-distilled water to a final concentration of 2.5 mg/ml.

Scanning Electron Microscopy—

A 30 µl suspension of 1 day aged peptide solution was dried at room temperature on a microscope glass cover slip and coated with gold. Scanning electron microscopy images were made using a JSM JEOL 6300 SEM operating at 20 kV.

Congo Red (CR) Staining and Birefringence—

A 10 µl suspension of a 1 day aged peptide solution was allowed to dry overnight on a glass microscope slide. Staining was performed by the addition of 10 µl solution of 80% ethanol saturated with CR and NaCl. The slide was allowed to dry for a few hours at room temperature. Birefringence was determined with a SZX-12 Stereoscope equipped with crosspolarizes.

Fourier Transform Infrared Spectroscopy—

Infrared spectra were recorded using Nicolet Nexus 470 FT-IR spectrometer with a DGTS detector. A 30 µl suspension of 1 day aged polypeptide solution was dried by vacuum on a $CaF_2$ plate to form thin film. The peptide deposits was resuspended in double distilled water and dried. The resuspension procedure was repeated twice to ensure maximal hydrogen to deuterium exchange. The measurements were taken using a 4 $cm^{-1}$ resolution and 2000 scans averaging. The transmittance minima values were determined by OMNIC analysis program (Nicolet).

Results

As shown in FIG. 19a structural analysis using SEM (scanning electron microscopy) showed that under similar conditions by which peptide nanotubes were formed by the diphenylalanine, tubular nanometric structures self-assembled by polyphenylalanine peptides of 50-136 amino acid residues. These nanometric particles existed as individual entities and their assembly was very efficient. The efficiency and homogeneity were similar to those observed with the peptide nanotubes self assembled by diphenylalanine peptides (see Example 1 above). Nanotubes of polyphenylalanine showed an apple green birefringence as seen upon Congo red staining and visualization under crossed polarized light (FIG. 19b). An amide I FT-IR spectrum of the polyphenylalanine solution exhibited a minimum at 1632 $cm^{-1}$ that is indicative of a parallel β-sheet structure (FIG. 19c). These properties are consistent with biophysical properties of peptide nanotubes self assembled by diphenylalanine peptides.

Example 4

Tubular nanostructures were formed from naphthylalanine-naphthylalanine (Nal-Nal) dipeptides, in accordance with preferred embodiment of the present invention. The Chemical structure of the Nal-Nal dipeptide is schematically shown in FIG. 20.

Fresh stock solutions of Nal-Nal dipeptides were prepared by dissolving lyophilized form of the peptides in 1,1,1,3,3,3-hexafluoro-2-propanol (HFIP, Sigma) at a concentration of 100 mg/mL. To avoid any pre-aggregation, fresh stock solutions were prepared for each experiment.

The peptides stock solutions were diluted into a final concentration of 2 mg/mL in double distilled water, then the samples were placed on 200 mesh copper grid, covered by carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.

FIG. 21 is an electron microscope image of the samples, captured a few minutes after the dilution of the peptide stock into the aqueous solution. As shown, the dipeptides form thin (from several nanometers to a few tens of nanometers in diameter) and elongated (several microns in length) tubular structures.

Example 5

Tubular and planar nanostructures were formed from by four different dipeptides, in accordance with preferred embodiment of the present invention.

The following dipeptides were used: (Pentafluoro-Phenylalanine)-(Pentafluoro-Phenylalanine), (Iodo-Phenylalanine)-(Iodo-Phenylalanine), (4-Phenyl phenylalanine)-(4-Phenyl phenylalanine) and (P-nitro-Phenylalanine)-(P-nitro-Phenylalanine).

For the first two dipeptides [(Pentafluoro-Phenylalanine)-(Pentafluoro-Phenylalanine) and (Iodo-Phenylalanine)-(Iodo-Phenylalanine)] fresh stock solutions were prepared by dissolving lyophilized form of the peptides in DMSO at a concentration of 100 mg/mL.

For the third and fourth dipeptides [(4-Phenyl phenylalanine)-(4-Phenyl phenylalanine) and (P-nitro-Phenylalanine)-(P-nitro-Phenylalanine)], fresh stock solutions were prepared by dissolving lyophilized form of the peptides in 1,1,1,3,3,3-hexafluoro-2-propanol (HFIP, Sigma) at a concentration of 100 mg/mL. To avoid any pre-aggregation, fresh stock solutions were prepared for each experiment.

The peptides stock solutions were diluted into a final concentration of 2 mg/mL in double distilled water.

In the case of (P-nitro-Phenylalanine)-(P-nitro-Phenylalanine) the final concentration was 5 mg/mL.

Subsequently, the samples were placed on 200 mesh copper grid, covered by carbon stabilized formvar film. Following 1 minute, excess fluid was removed and the grid was negatively stained with 2% uranyl acetate in water. Following 2 minutes of staining, excess fluid was removed from the grid. Samples were viewed in JEOL 1200EX electron microscope operating at 80 kV.

FIGS. 22A-D are electron microscope images of the four samples, captured a few minutes after the dilution of the peptide stock into the aqueous solution.

FIG. 22A shows tubular assemblies formed by the (Pentafluoro-Phenylalanine)-(Pentafluoro-Phenylalanine) dipeptide, FIG. 22B shows tubular structures assembled by (Iodo-Phenylalanine)-(Iodo-Phenylalanine), FIG. 22 C shows planar nanostructures formed by (4-Phenyl phenylalanine)-(4-Phenyl phenylalanine), and FIG. 22D shows fibrilar assemblies of (P-nitro-Phenylalanine)-(P-nitro-Phenylalanine).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition comprising:
   (i) a tubular or spherical nanostructure being composed of a plurality of peptides, wherein each of said plurality of peptides includes aromatic homodipeptides or wherein each of said plurality of peptides includes no more than 4 amino acids and comprises Phe-Phe; and
   (ii) an agent being attached to said tubular or spherical nanostructure.

2. The composition of claim 1, wherein said agent is selected from the group consisting of a drug, a nucleic acid molecule and a polypeptide.

3. The composition of claim 1, wherein said agent is capable of being slowly released from said nanostructure.

4. The composition of claim 1, wherein said aromatic moiety is selected from the group consisting of substituted or unsubstituted naphthalenyl and substituted or unsubstituted phenyl.

5. The composition of claim 1 wherein said substituted phenyl is selected from the group consisting of pentafluoro phenyl, iodophenyl, biphenyl and nitrophenyl.

6. The composition of claim 1, wherein said homodipeptide is selected from the group consisting of naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

7. A composition comprising a matrix and a plurality of nanostructures dispersed throughout said matrix, said nanostructure being composed of a plurality of peptides, wherein each of said plurality of peptides includes aromatic homodipeptides or wherein each of said plurality of peptides includes no more than 4 amino acids and comprises Phe-Phe.

8. The composition of claim 7, wherein said matrix is selected from the group consisting of a metal matrix, a ceramic matrix and a polymeric matrix.

9. The composition of claim 7, wherein said nanostructure is coated by a conductive material.

10. The composition of claim 7, wherein said matrix is a two-dimensional matrix or a three-dimensional matrix.

11. The composition of claim 7, wherein said aromatic moiety is selected from the group consisting of substituted or unsubstituted naphthalenyl and substituted or unsubstituted phenyl.

12. The composition of claim 7 wherein said substituted phenyl is selected from the group consisting of pentafluoro phenyl, iodophenyl, biphenyl and nitrophenyl.

13. The composition of claim 7, wherein said homodipeptide is selected from the group consisting of naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

14. A nanofluid comprising nanostructures suspended in a fluid, wherein at least a portion of said nanostructures is composed of a plurality of peptides, wherein each of said plurality of peptides includes aromatic homodipeptides or wherein each of said plurality of peptides includes no more than 4 amino acids and comprises Phe-Phe.

15. The nanofluid of claim 14, wherein said nanostructure is coated by a conductive material.

16. The nanofluid of claim 14, wherein said aromatic moiety is selected from the group consisting of substituted or unsubstituted naphthalenyl and substituted or unsubstituted phenyl.

17. The nanofluid of claim 14, wherein said substituted phenyl is selected from the group consisting of pentafluoro phenyl, iodophenyl, biphenyl and nitrophenyl.

18. The nanofluid of claim 14, wherein said homodipeptide is selected from the group consisting of naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

19. A field emitter device, comprising an electrode and a nanostructure being composed of a plurality of peptides, said electrode and said nanostructure being designed and constructed such that when an electrical field is formed therebetween, electrons are emitted from said nanostructure, wherein each of said plurality of peptides includes aromatic homodipeptides or wherein each of said plurality of peptides includes no more than 4 amino acids and comprises Phe-Phe.

20. The device of claim 19, further comprising a substrate having a fluorescent powder coating, said fluorescent powder coating being capable of emitting light upon activation by said electrons.

21. The device of claim 19, wherein said nanostructure is coated by a conductive material.

22. The device of claim 19, wherein said aromatic moiety is selected from the group consisting of substituted or unsubstituted naphthalenyl and substituted or unsubstituted phenyl.

23. The device of claim 19, wherein said substituted phenyl is selected from the group consisting of pentafluoro phenyl, iodophenyl, biphenyl and nitrophenyl.

24. The device of claim 19, wherein said homodipeptide is selected from the group consisting of naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

25. An apparatus for electron emission lithography, comprising:
(a) an electron emission source being at a first electrical potential, said electron emission source including at least one nanostructure being composed of a plurality of peptides, wherein each of said plurality of peptides includes aromatic homodipeptides or wherein each of said plurality of peptides includes no more than 4 amino acids and comprises Phe-Phe; and
(b) an electrically conducting mounting device being in a second electrical potential, said second electrical potential being different than said first electrical potential;
wherein a difference between said second electrical potential and said first electrical potential is selected such that electrons are emitted from said electron emission source, and impinge on said mounting device to thereby perform a lithography process on a sample mounted on said mounting device.

26. The apparatus of claim 25, further comprising a magnetic field generator for generating a magnetic field, thereby to direct said electrons to a predetermined location on said sample.

27. The apparatus of claim 25, wherein said nanostructure is coated by a conductive material.

28. The apparatus of claim 25, wherein said aromatic moiety is selected from the group consisting of substituted or unsubstituted naphthalenyl and substituted or unsubstituted phenyl.

29. The apparatus of claim 25, wherein said substituted phenyl is selected from the group consisting of pentafluoro phenyl, iodophenyl, biphenyl and nitrophenyl.

30. The apparatus of claim 25, wherein said homodipeptide is selected from the group consisting of naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

31. An electronic inverter having a first switching device and a second switching device, each of said first switching device and said first switching device comprising a source electrode, a drain electrode, a gate electrode and a channel, such that said drain electrode of said first switching device is electrically communicating with said source electrode of said second switching device, wherein at least one of said gate electrode and said channel comprises a nanostructure being composed of a plurality of peptides, wherein each of said plurality of peptides includes aromatic homodipeptides or wherein each of said plurality of peptides includes no more than 4 amino acids and comprises Phe-Phe.

32. The electronic inverter of claim 31, wherein said nanostructure is a tubular nanostructure.

33. The electronic inverter of claim 31, wherein said source electrode and said drain electrode are formed on a substrate.

34. The electronic inverter of claim 33, wherein said substrate comprises a thermal oxide deposited over a silicon substrate.

35. The electronic inverter of claim 31, wherein said nanostructure is coated by a conductive material.

36. The electronic inverter of claim 31, wherein said aromatic moiety is selected from the group consisting of substituted or unsubstituted naphthalenyl and substituted or unsubstituted phenyl.

37. The electronic inverter of claim 31, wherein said substituted phenyl is selected from the group consisting of pentafluoro phenyl, iodophenyl, biphenyl and nitrophenyl.

38. The electronic inverter of claim 31, wherein said homodipeptide is selected from the group consisting of naphthylalanine-naphthylalanine dipeptide, (pentafluoro-phenylalanine)-(pentafluoro-phenylalanine) dipeptide, (iodo-phenylalanine)-(iodo-phenylalanine) dipeptide, (4-phenyl phenylalanine)-(4-phenyl phenylalanine) dipeptide and (p-nitro-phenylalanine)-(p-nitro-phenylalanine) dipeptide.

39. A nanofluid comprising nanostructures suspended in a fluid, wherein at least a portion of said nanostructures is composed of a plurality of peptides, wherein each of said plurality of peptides includes aromatic homodipeptides or wherein each of said plurality of peptides includes no more than 4 amino acids and comprises Phe-Phe.

\* \* \* \* \*

```
                        SEQUENCE LISTING

<160> NUMBER OF SEQ ID NOS: 17

<210> SEQ ID NO 1
<211> LENGTH: 2
<212> TYPE: PRT
<213> ORGANISM: Artificial sequence
<220> FEATURE:
<223> OTHER INFORMATION: Synthetic peptide

<400> SEQUENCE: 1

Phe Phe
1

<210> SEQ ID NO 2
<211> LENGTH: 2
<212> TYPE: PRT
<213> ORGANISM: Artificial sequence
<220> FEATURE:
<223> OTHER INFORMATION: Synthetic peptide

<400> SEQUENCE: 2

Trp Trp
1

<210> SEQ ID NO 3
<211> LENGTH: 2
<212> TYPE: PRT
<213> ORGANISM: Artificial sequence
<220> FEATURE:
<223> OTHER INFORMATION: Synthetic peptide

<400> SEQUENCE: 3

Trp Tyr
1

<210> SEQ ID NO 4
<211> LENGTH: 2
<212> TYPE: PRT
<213> ORGANISM: Artificial sequence
<220> FEATURE:
<223> OTHER INFORMATION: Synthetic peptide

<400> SEQUENCE: 4

Trp Phe
1

<210> SEQ ID NO 5
<211> LENGTH: 2
<212> TYPE: PRT
<213> ORGANISM: Artificial sequence
```

-continued

```
<220> FEATURE:
<223> OTHER INFORMATION: Synthetic peptide

<400> SEQUENCE: 5

Phe Trp
1

<210> SEQ ID NO 6
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: Phenylglycine

<400> SEQUENCE: 6

Xaa Xaa
1

<210> SEQ ID NO 7
<211> LENGTH: 3
<212> TYPE: PRT
<213> ORGANISM: Artificial sequence
<220> FEATURE:
<223> OTHER INFORMATION: Synthetic peptide

<400> SEQUENCE: 7

Cys Phe Phe
1

<210> SEQ ID NO 8
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: D stereoisomer

<400> SEQUENCE: 8

Phe Phe
1

<210> SEQ ID NO 9
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: naphthylalanine

<400> SEQUENCE: 9

Xaa Xaa
1

<210> SEQ ID NO 10
<211> LENGTH: 2
<212> TYPE: PRT
<213> ORGANISM: Artificial sequence
<220> FEATURE:
<223> OTHER INFORMATION: Synthetic peptide
```

-continued

```
<220> FEATURE:
<221> NAME/KEY: MOD_RES
<222> LOCATION: (1)..(2)
<223> OTHER INFORMATION: pentafluro-phenylalanine

<400> SEQUENCE: 10

Xaa Xaa
1

<210> SEQ ID NO 11
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: iodo-phenylalanine

<400> SEQUENCE: 11

Xaa Xaa
1

<210> SEQ ID NO 12
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: 4-phenyl phenylalanine

<400> SEQUENCE: 12

Xaa Xaa
1

<210> SEQ ID NO 13
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(2)
<223> OTHER INFORMATION: p-nitro-phenylalanine

<400> SEQUENCE: 13

Xaa Xaa
1

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Lys Leu Val Phe Phe Ala Glu
1               5

<210> SEQ ID NO 15
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 15

Lys Leu Val Phe Phe
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide

<400> SEQUENCE: 16

Leu Val Phe Phe Ala
1               5

<210> SEQ ID NO 17
<211> LENGTH: 42
<212> TYPE: PRT
<213> ORGANISM: Artificial Sequence
<220> FEATURE:
<223> OTHER INFORMATION: Synthetic peptide

<400> SEQUENCE: 17

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```